United States Patent
Windeyer et al.

(10) Patent No.: US 8,554,372 B2
(45) Date of Patent: Oct. 8, 2013

(54) SYSTEM AND METHOD FOR HISTOLOGICAL TISSUE SPECIMEN PROCESSING

(75) Inventors: Victor Camfield Windeyer, Mosman (AU); Michael Houston Drummond, Glen Waverley (AU)

(73) Assignee: Leica Biosystems Melbourne Pty Ltd, Mount Waverley (AU)

( * ) Notice: Subject to any disclaimer, the term of this patent is extended or adjusted under 35 U.S.C. 154(b) by 1071 days.

(21) Appl. No.: 10/573,856

(22) PCT Filed: Sep. 29, 2004

(86) PCT No.: PCT/AU2004/001337
§ 371 (c)(1), (2), (4) Date: Feb. 26, 2007

(87) PCT Pub. No.: WO2005/031312
PCT Pub. Date: Apr. 7, 2005

(65) Prior Publication Data
US 2007/0243626 A1    Oct. 18, 2007

(30) Foreign Application Priority Data
Sep. 29, 2003   (AU) .................. 2003905301

(51) Int. Cl.
*G01N 1/31* (2006.01)

(52) U.S. Cl.
USPC ............... 700/266; 700/100; 700/101; 422/3; 422/105; 422/62; 435/3; 435/286.1; 435/286.2; 435/286.3; 435/286.4; 435/286.5; 435/286.6; 435/286.7; 435/284.1; 435/4; 436/50; 436/55; 702/19; 702/22; 702/31; 702/32

(58) Field of Classification Search
USPC .......... 702/19, 22, 31, 32; 700/100, 101, 266; 422/3, 105; 435/3, 286.1–286.7, 284.1; 436/50, 55
See application file for complete search history.

(56) References Cited

U.S. PATENT DOCUMENTS

| | | | |
|---|---|---|---|
| 3,301,318 A | 1/1967 | Haake | |
| 3,889,014 A | 6/1975 | Kinney et al. | |

(Continued)

FOREIGN PATENT DOCUMENTS

| | | |
|---|---|---|
| DE | 199 52 349 A1 | 6/2000 |
| EP | 0 753 745 A2 | 1/1997 |

(Continued)

OTHER PUBLICATIONS

Supplementary European Search Report issued Apr. 15, 2009 for European Application No. EP 02 78 7194.

(Continued)

*Primary Examiner* — Jill Warden
*Assistant Examiner* — Shogo Sasaki
(74) *Attorney, Agent, or Firm* — Sughrue Mion, PLLC

(57) ABSTRACT

A method of managing resources of a histological tissue processor, the tissue processor comprising at least one retort (12, 14) selectively connected for fluid communication to at least one of a plurality of reagent resources (26) by a valve mechanism (40), the method comprising the step of: nominating resources according to one of: group, where a group nomination corresponds to a resource's function; type, where a type nomination corresponds to one or more attributes of a resource within a group; station, where a station nomination corresponds to a point of supply of a resource.

14 Claims, 28 Drawing Sheets

(56) References Cited

U.S. PATENT DOCUMENTS

| | | | |
|---|---|---|---|
| 3,892,197 A | | 7/1975 | Kinney et al. |
| 4,141,312 A | | 2/1979 | Louder et al. |
| 4,483,270 A | | 11/1984 | Toya et al. |
| 4,729,876 A | | 3/1988 | Hennessy et al. |
| 4,911,915 A | | 3/1990 | Fredenburgh |
| 5,049,510 A | | 9/1991 | Repasi |
| 5,084,133 A | | 1/1992 | Guy et al. |
| 5,158,895 A | * | 10/1992 | Ashihara et al. ............ 436/526 |
| 5,282,149 A | * | 1/1994 | Grandone et al. ............. 702/19 |
| 5,357,095 A | | 10/1994 | Weyrauch et al. |
| 5,437,838 A | * | 8/1995 | DeMoranville et al. ........ 422/67 |
| 5,725,835 A | | 3/1998 | Lautenschlager |
| 5,839,091 A | | 11/1998 | Rhett et al. |
| 6,048,722 A | * | 4/2000 | Farb et al. .................. 435/287.1 |
| 6,096,561 A | | 8/2000 | Tayi |
| 2001/0003652 A1 | | 6/2001 | Freeman |
| 2001/0029320 A1 | * | 10/2001 | Trumbull et al. ............. 600/300 |
| 2001/0051365 A1 | | 12/2001 | Morales et al. |
| 2001/0055799 A1 | | 12/2001 | Baunoch et al. |
| 2002/0131896 A1 | | 9/2002 | Hunnell et al. |
| 2008/0220468 A1 | | 9/2008 | Windeyer et al. |

FOREIGN PATENT DOCUMENTS

| | | |
|---|---|---|
| GB | 2 334 688 A | 9/1999 |
| JP | 63-144258 A | 6/1988 |
| JP | 03-068865 A | 3/1991 |
| JP | 03-068866 A | 3/1991 |
| JP | 11-502926 | 3/1999 |
| JP | 11-271194 A | 10/1999 |
| JP | 11-513123 A | 11/1999 |
| JP | 2001-194276 | 7/2001 |
| RU | 2 104 513 C1 | 10/1998 |
| SU | 1 317 307 | 6/1987 |
| WO | 86/06479 A1 | 11/1986 |
| WO | 93/19207 | 9/1993 |
| WO | 98/25140 A1 | 6/1998 |
| WO | 99/09390 A1 | 2/1999 |
| WO | 00/36393 A2 | 6/2000 |
| WO | 00/47975 A1 | 8/2000 |
| WO | 01/31347 A1 | 5/2001 |
| WO | 01/44783 A1 | 6/2001 |
| WO | WO 03/029845 A2 | 4/2003 |

OTHER PUBLICATIONS

Willis, Donna. " Microwave Tissue Processing," EBSciences Company, Nov. 1997, 3 pp. Retrieved Mar. 5, 2003, from www.ebsciences.com/staining/biopsy.htm.

Sutton, R. "Simple Distillation Laboratory #1 Chemistry 220," Lab Notes, School of Chemistry, Kalamazoo Valley Community College, Michigan, Aug. 30, 2001, 2 pp.. Retrieved Mar. 5, 2003, from http://puma.kvcc.edu/rsutton/C220/simple_distillation.htm.

"Tissue Processing," Medical Library, Univ. of Utah, Histology, School of Medicine, Utah, Dec. 6, 1988, 2 pp. Retrieved Mar. 5, 2003, from www.medlib.med.utah.edu/WebPath/HISTHTML/HISTOTCH/HISTOTCH.html.

"TPC 15 Tissue Processing Center," Medite Company Site, catalog of products, first version published Feb. 21, 2001, 4 pp. Retrieved Mar. 5, 2003, from www.medite.de/englisch/geraeteprogramm/geraeteprogramm/tissue-processing_centerhtm.

European Search Report dated May 7, 2012 issued in European patent application No. 11190008.0.

* cited by examiner

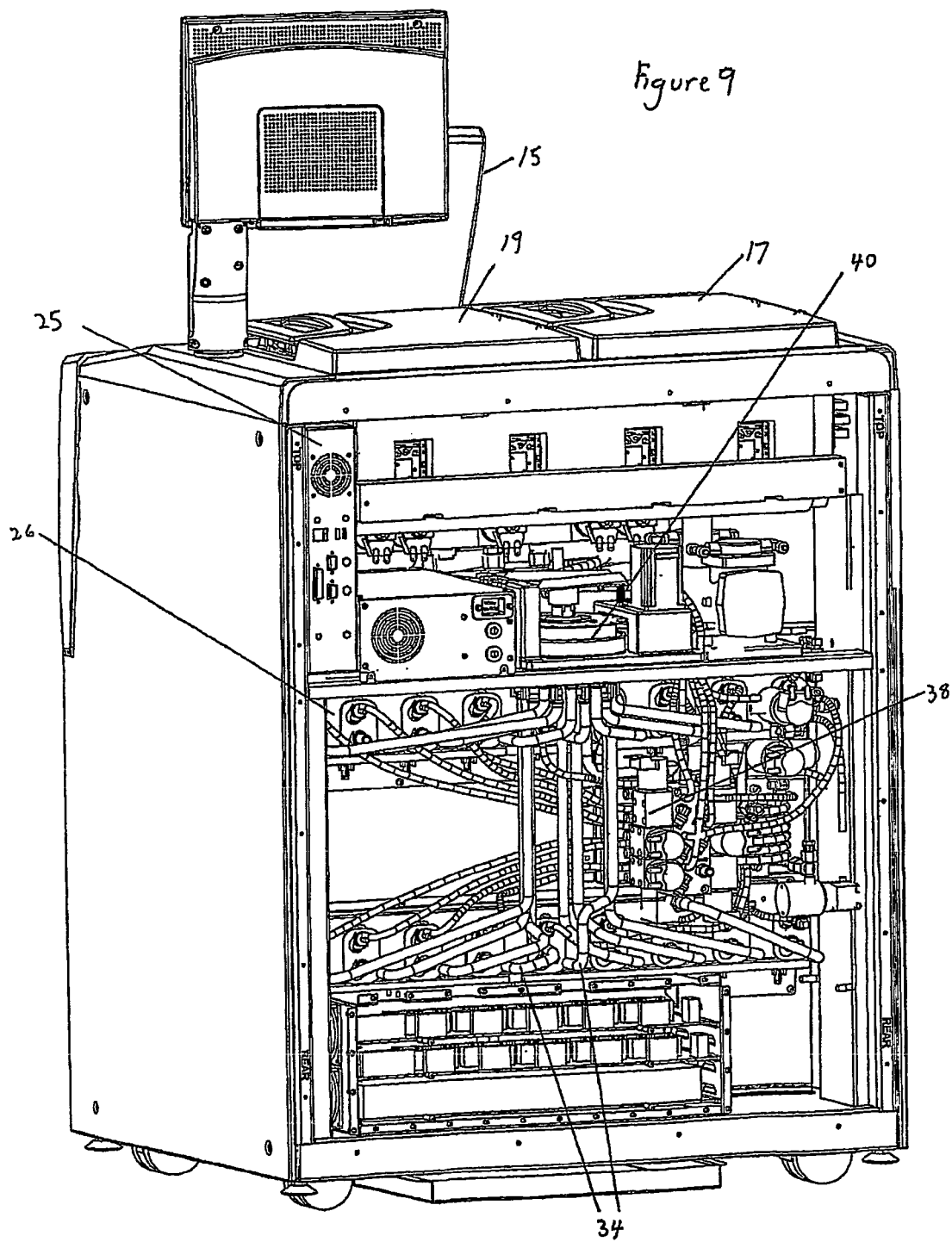

SYSTEM AND METHOD FOR HISTOLOGICAL TISSUE SPECIMEN PROCESSING

RELATED APPLICATIONS

This application claims priority to Australian Provisional Patent Application No. 2003905301, filed 29 Sep. 2003 entitled "System and Method for Histological Tissue Specimen Processing" and, the specification thereof is incorporated herein by reference in its entirety and for all purposes.

FIELD OF INVENTION

The present invention relates to a system and method for processing histological tissue specimens. In one form the invention relates to a system and method for tissue processing with the use of an automated tissue processor as disclosed in International Patent Application No PCT/AU02/01337, publication No WO 03/029845 titled "Histological Tissue Specimen Treatment" in the name of the present applicant and, it will be convenient to hereinafter describe the invention in relation to the dual retort tissue processor disclosed in that application. It should be appreciated, however, that the invention is not limited to that application, only. For example, in other forms the present invention may be applicable to tissue processors that are different from that disclosed in WO 03/029845, such as for example, tissue processors comprising a single retort.

BACKGROUND OF INVENTION

Throughout this specification the use of the word "inventor" in singular form may be taken as reference to one (singular) or all (plural) inventors of the present invention.

The inventor has identified the following related art.

Histological tissue specimen preparation is a physical process that involves chemical solutions reacting with biological specimens. The end result of such treatment is a sample that has had water removed, and been infiltrated with paraffin. Once the tissue has been embedded in the paraffin, it is stable and may then be sectioned on a rotary microtome. This process typically involves four different sub-procedures:

(a) Fixation

Fixation is a process by means of which cell proteins are stabilised, and the process is normally performed using chemical solutions. A good fixative is usually a fluid, which will neither shrink nor swell the tissue, and more particularly will not dissolve its constituent parts, but will kill bacteria and moulds, and render enzymes inactive. In addition, the solution must modify tissue constituents in such a way that they retain their form when subjected to treatment that would have damaged them in their initial state. The most commonly used chemical solution is Formalin.

(b) Dehydration

Since the ultimate purpose of tissue specimen treatment is to embed the tissue sample in paraffin, and since water and paraffin are not miscible, the sample must be dehydrated after the fixation step. This is usually achieved by subjecting the tissue sample to increasing concentrations of alcohols.

(c) Clearing

After dehydration, the tissue sample is still not capable of accepting paraffin since paraffin and alcohol are not miscible. A chemical solution, selected to be miscible with both alcohol and paraffin, is used to clear the alcohol from the sample. The chemical solution most commonly used is Xylene. Unfortunately, Xylene is considered to be toxic although most histological processing laboratories use Xylene on a daily basis.

(d) Infiltration

The fourth and final step in the tissue sample treatment is infiltrating the sample, usually with paraffin wax. In this step the cleared tissue samples are placed into paraffin heated to a few degrees above its liquefaction temperature. Several changes of paraffin may be required to remove the residual Xylene so that the tissue is completely infiltrated with the molten paraffin.

The timing of the fluid change for all the fluids relates to the requirement to effectively displace the previous chemical from the tissue samples. Tissue samples can vary considerably in content and size, and therefore there may be a large variation in the time required to displace the fluid from one sample compared to the time taken to displace fluid from another. Further, some samples are sandwiched between biopsy pads that are porous and absorb significant quantities of fluid.

An attempt at automation of the previously manual method of tissue processing involved placing solutions in a circular arrangement so that samples could be moved from container to container until they reached the last heated paraffin reservoir. An example of an instrument with this type of configuration used in the histology field was the Technicon™ instrument. One of the major disadvantages of instruments of this type was that they allowed fumes to escape into the laboratory, thus exposing the laboratory workers to a hazardous environment. To overcome this problem, the next generation of tissue processing instruments included a centrally located closed chamber for the tissue samples. The solutions necessary for tissue processing were delivered into the closed chamber where the fluids are pumped in and out of the chamber in sequence. Normally the chamber would not be opened during the process.

Tissue processing may be broken into sequential steps as mentioned above. The particular fluids used, temperatures and times of exposure may be defined in a protocol.

As the chamber is closed, and only a single protocol can be run, the protocol must attempt to cater for the range of tissue samples that may be included in a single run. This can result in either over processing or under processing of some samples. Given the sealed nature of the retort, tissue samples may not easily be removed or added during a processing run.

Another problem is that some samples require urgent processing, while other samples are not urgent. In the known tissue sample preparation apparatus it has not been possible to stop a current sample run to process a sample required urgently, or to employ a protocol that allows an urgently required sample to be processed with other samples that require longer processing times. Thus, either the urgently required sample is run in isolation, or it is put with other samples, increasing the processing time.

Examples of known automated tissue processing machines will be found in the patent literature, and typical examples include U.S. Pat. No. 4,141,312 Louder, and U.S. Pat. No. 5,049,510 Repasi et al.

The prior art has therefore been unable to deal adequately with ensuring that a variety of samples can be processed safely and efficiently and, in quantities that satisfy the needs of modern laboratories. It would also be desirable to effectively shorten the time taken to process tissue samples thus, increasing throughput.

Some systems include heating of wax or tissue samples with microwaves, however microwave systems are difficult to automate, and preferentially heat the tissue sample rather than the reagents. These systems are known to be able to process up to only about 80 tissue cassettes in a run. Lower throughputs are due, in part, to the limitations introduced by the need to supply power to the microwave source.

Any discussion of documents, devices, acts or knowledge in this specification is included to explain the context of the invention. It should not be taken as an admission that any of the material formed part of the prior art base or the common general knowledge in the relevant art on or before the priority date of the invention disclosed herein, being the subject of the appended claims.

SUMMARY OF INVENTION

In one aspect the present invention provides a method of managing resources of a histological tissue processor, the tissue processor comprising at least one retort selectively connected for fluid communication to at least one of a plurality of reagent resources by a valve mechanism, the method comprising the step of: nominating resources according to one of:

group, where a group nomination corresponds to a resource's function;

type, where a type nomination corresponds to one or more attributes of a resource within a group;

station, where a station nomination corresponds to a point of supply of a resource.

Preferably, a group comprises reagents that function as one of the following:
fixative;
dehydrant;
defatter;
clearer;
wax;
cleaning solvent;
cleaning alcohol;
cleaning water.

Further, it is preferable that type attributes comprise one or more of:
reagent group;
reagent name;
nominal reagent concentration;
nominal reagent concentration thresholds;
reagent use threshold;
reagent temperature thresholds.

In a preferred embodiment, the corresponding point of supply of a resource comprises one or more of the following attributes:
reagent group;
reagent type;
reagent name;
reagent container;
reagent status;
reagent use history;
reagent use threshold;
reagent concentration history;
reagent concentration threshold;
reagent temperature thresholds In another aspect, the present invention provides a method of determining availability of resources of a histological tissue processor, the tissue processor comprising at least one retort selectively connected for fluid communication to at least one of a plurality of reagent resources by a valve mechanism, the method comprising the steps of: predetermining steps for at least one tissue processing protocol; nominating resources required by the predetermined protocol steps in accordance with a selection methodology; for all nominated resources, setting a nominated resource as unavailable if the resource fails to meet a first predetermined operating criteria when the resource is scheduled for use by the predetermined protocol steps; determining a user requirement comprising one of a schedule mode and a run time mode; setting nominated resources that meet the first predetermined operating criteria and fail to meet further predetermined operating criteria corresponding to the determined user requirement as unavailable; setting all remaining nominated resources as available.

In a preferred embodiment, the selection methodology comprises a method of managing resources in which the resources are nominated according to one of group, type or station, as disclosed above.

The first predetermined operating criteria may comprise a station being in a full state such that the station holds sufficient reagent to fill a retort. At this point a user requirement of either a schedule mode or a run time mode is determined. Accordingly, the further predetermined operating criteria corresponding to the determined user requirement may comprise any one or more of the following as indicated:

in run time mode, a station being in a full state such that the station holds sufficient reagent to fill a retort;

in schedule mode, a station not being used in a preceding protocol step;

in run time mode, a station not being previously used in two sequential protocol steps;

in schedule mode, a station not holding the purest reagent;

in either schedule or run time mode, a station holding a reagent that has equal or greater purity than the reagent of a station used in the preceding protocol step;

a station with a reagent not exceeding a temperature threshold for a given protocol step;

a station with a reagent not exceeding a threshold of one of purity, number of tissue cassettes treated, protocol cycles or, age.

In a further aspect, the present invention provides a method of selecting a resource of a histological tissue processor, the tissue processor comprising at least one retort selectively connected for fluid communication to at least one of a plurality of reagent resources by a valve mechanism, the method comprising the steps of: determining the availability of one or more of the plurality of resources; determining the status of a tissue processing protocol step within a tissue processing protocol based on a resource selection methodology; determining at least one characteristic of the plurality of resources; selecting an available resource in accordance with a predetermined selection criteria wherein the predetermined selection criteria is based on the determined status of the tissue processing protocol step and the determined resource characteristic.

The step of determining the availability of one or more of the plurality of resources preferably comprises a method of determining availability of resources as disclosed above.

In one embodiment, the status of a tissue processing protocol step may comprise the order of occurrence of the protocol step with the protocol.

In one embodiment, the step of determining at least one characteristic of the plurality of resources may comprise determining the purity of a reagent. In another embodiment, the step of determining at least one characteristic of the plurality of resources may comprise determining the number of cassettes processed. In a preferred embodiment, the step of determining at least one characteristic of the plurality of resources may comprise determining the purity of a reagent in accordance with the following steps:

upon running a tissue processing protocol, estimate a carry over volume for each reagent component according to:

$$V_{CO}=(N_b \times C_b)+(N_c \times C_c)+(N_p \times N_c \times C_p)+V_{cr}$$

where
$V_{CO}$=volume of carry over (ml)
$N_b$=number of baskets per retort
$C_b$=carry over per basket (ml)
$N_c$=number of cassettes
$C_c$=carry over per cassette (ml)
$N_p$=number of biopsy pads per cassette
$C_p$=carry over per biopsy pad (ml)
$V_{cr}$=carry over for an empty retort (ml),
after each retort fill, estimate the carry over amount in a reagent container for each reagent component according to:

$$V_{pc}=(P_p \times V_{CO})/1000$$

where
$V_{pc}$=volume of a reagent component carried over from a previous reagent container
$P_p$=proportion of reagent component in previous reagent container,
after each retort fill, estimate the volume of each reagent component according to:

$$V_{af}=V_{pc}+(V_b \times P_{bf})$$

where
$V_{af}$=volume of reagent component in the reagent container after retort fill
$P_{bf}$=proportion of reagent component in reagent container before retort fill
$V_b$=volume available in reagent container
after each retort fill, estimate the proportion of each reagent component in the reagent container according to:

$$P_{af}=V_{af}/V_b$$

where,
$P_{af}$=proportion of reagent component in the reagent container after retort fill,
after each retort fill nominate a selected reagent component as a primary component and return $P_{af}$ as the purity of the primary component.

Further included, by a preferred embodiment, in the above method of selecting resources is the step of updating reagent properties of a station according to the following:

a) requesting the following information from a user of the tissue processor:
confirmation that the user wishes to change a reagent in a given station;
reagent group;
reagent type;
station purity;
station status;
b) updating reagent properties according to the information provided in step a).

It is preferable to also further include the step of:
initiating a system request at regular intervals to determine whether a station's reagent has been removed;
informing a user when a reagent has been replaced and performing steps a) and b) disclosed above.

In yet another embodiment of the method of selecting resources, it is preferable to further include a method of resolving conflict between protocol steps allocated respectively to the retorts of a tissue processor comprising at least two retorts, the method comprising the steps of:
determining a priority for each tissue processing protocol;
selectively modifying at least one protocol step of at least one of the tissue processing protocols based on the determined priority.

The following steps may also be carried out, specifically, the steps of:
assigning a first tissue processing protocol with a highest priority;
assigning at least one second tissue processing protocol with a lower priority; and
fixing the protocol steps of the highest priority protocol so as to remain unmodified.

The step of selectively modifying at least one protocol step disclosed above may comprise lengthening the duration of at least one protocol step of the lower priority tissue processing protocol(s). In another embodiment, the step of selectively modifying at least one protocol step disclosed above may comprise lengthening the duration of at least one protocol step of the higher priority tissue processing protocol(s)

Furthermore, the step of selectively modifying at least one protocol step may comprise shortening the duration of at least one protocol step of the lower priority tissue processing protocol(s). At least one protocol step, other than the protocol step selectively modified, may be correspondingly modified such that the total duration of each tissue processing protocol remains unmodified. The at least one protocol step may be selectively modified within predetermined limits.

Further to the above disclosed method of selecting resources, the method may further comprise scheduling two or more tissue processing protocols comprising the steps of: determining single protocol schedules for each individual tissue processing protocol comprising the steps of; allocating a user defined reference time point; determining a sequence of protocol steps in accordance with a logical progression of actions based on one or more of; a start time, an end time and a duration of each protocol step; allocating resources for use in accordance with at least one protocol step; determining a multiple protocol schedule comprising the steps of: combining two or more single protocol schedules wherein the two or more single protocol schedules overlap in time; resolving conflict between protocol steps of the two or more single protocol schedules in accordance with a method of resolving conflict as disclosed above.

In the above scheduling steps, the user defined reference time point may be one of:
a protocol start time;
a protocol end time;
a protocol step start time; and
a protocol step end time.

Each of the protocol steps disclosed above may comprise performing any one of the following:
fixation;
dehydration;
defatting;
clearing;
infiltration;
cleaning;
drying;
concluding protocol.

A protocol schedule determined in accordance with the method disclosed above may be displayed to a user for confirmation.

In yet another aspect the present invention provides a method of managing thermal resources of a histological tissue processor, the tissue processor comprising at least one retort in operative connection with thermal resources for accelerating tissue processing steps and the at least one retort further selectively connected for fluid communication to at least one of a plurality of reagent resources by a valve mechanism, the method comprising the steps of:

a) evaluating existing system heating power states of the thermal resources comprising the steps of:
retrieving existing heating power states of the thermal resources;
determining whether one or more thermal resources has signalled a heating power request;
selecting a corresponding heating power setting for each signalled heating power request;
b) delegating system heating power comprising the steps of:
determining updated thermal resource heating power states in accordance with a first predetermined criteria;
allocating heating power to the thermal resources in accordance with a second predetermined criteria wherein the second predetermined criteria is based on the updated thermal resource heating power states.

A signalled heating power request may comprises one of: a ramping power request and; a maintaining power request.

The heating power setting for a ramping power request may be selected from a heating power table. Also, the heating power setting for a maintaining power request may be selected from a steady state power table. In one embodiment, the thermal resources may be thermal resources of a first and second retort of the tissue processor.

In a preferred form, a tissue processor comprising at leat two retorts is operated in accordance with the method of managing thermal resource heating power wherein the first predetermined criteria may comprise:
both first and second retorts' thermal resources ramping;
first retort's thermal resources ramping, second retort's thermal resources on;
first retort's thermal resources on, second retort's thermal resources ramping;
both first and second retorts' thermal resources on;
first retort's thermal resources ramping, second retort's thermal resources off;
first retort's thermal resources off, second retort's thermal resources ramping;
both first and second retorts' thermal resources off.

The second predetermined criteria in the method of managing thermal resource heating power may comprise: a proportional share of heating power such that the proportional share of heating power is normalised for each thermal resource.

The thermal resources may comprise heaters for one or more of the following:
a retort;
a retort valve;
a wax bath;
a wax fluid line;
a wax valve.

In yet a further aspect, the present invention provides a method of controlling heaters of a selected component of a tissue processor for decreasing heat up times of the component and accelerating tissue processing steps, the tissue processor comprising at least one retort selectively connected for fluid communication to at least one of a plurality of reagent resources by a valve mechanism, the method comprising the steps of:
ascertaining at least one of a plurality of temperature readings from each tissue processor component;
determining the fill state of the selected component;
selecting a predetermined heater control algorithm based on at least one or more of:
the number of ascertained temperature readings;
the location at which the temperature of temperature readings is measured;
the determined fill state of the selected component.

The selected component may be one of a retort and a wax bath.

In one embodiment, the predetermined heater control algorithm is one of:
a liquid control algorithm;
a liquid sensor control algorithm;
a heater mat control algorithm;
a heater mat sensor control algorithm.

The heater mat control algorithm and the heater mat sensor control algorithm may be one and the same algorithm. Each temperature sensing module may be operatively associated with a retort and may further comprise at least two individual temperature sensing elements. Furthermore, the temperature sensing modules may comprise temperature sensing elements located at one or more of:
a wall of a retort, and:
at least one heating device operatively connected to a retort for heating the retort and its contents.

The selected predetermined heater control algorithm may comprise the step of turning heaters off if no evaluated temperature readings are returned.

In yet a further aspect the present invention provides a method of accelerating the processing of histological tissue samples comprising the steps of:
sensing the temperature of a selected component of a tissue processor with a first temperature sensor operatively connected to the selected component;
heating the selected component with at least one heating device operatively connected to the selected component;
wherein the at least one heating device is maintained at a temperature at or above a desired operating temperature of the selected component until the first temperature sensor senses the desired operating temperature.

The above method of accelerating the processing of histological tissue samples may further comprise the step of:
sensing the temperature of the at least one heating device with a second temperature sensor operatively connected to the at least one heating device so as to allow the at least one heating device to be operated at its maximum operating temperature in order to minimise the time required for the at least one heating device to heat the selected component to the desired operating temperature.

Preferably, the selected component of the tissue processor may be any one or more of:
one or more tissue processing retorts;
one or more tissue processing retort valves;
one or more tissue processing wax storage baths;
one or more tissue processing fluid lines connecting one or more retorts and wax storage baths.

The present invention also provides in other aspects a method of scheduling tissue processing protocols of a histological tissue processor, the tissue processor comprising at least two retorts selectively connected for fluid communication to at least one of a plurality of reagent resources by a valve mechanism, the method comprising resolving conflict between protocol steps allocated respectively to the retorts, comprising the steps of:
determining a priority for each tissue processing protocol;
selectively modifying at least one protocol step of at least one of the tissue processing protocols based on the determined priority.

Furthermore, the present invention also provides in other aspects a method of scheduling tissue processing protocols of a histological tissue processor, the tissue processor comprising at least two retorts selectively connected for fluid communication to at least one of a plurality of reagent resources by a valve mechanism, the method comprising the steps of:

allocating a tissue processing protocol to each respective retort;

assigning a priority for each allocated tissue processing protocol;

selectively modifying at least one protocol step of the tissue processing protocol assigned with a lower priority.

Additionally, the present invention also provides in other aspects a method of managing reagent resources of a histological tissue processor, the tissue processor comprising at least one retort selectively connected for fluid communication to at least one of a plurality of reagent resources by a valve mechanism, the method comprising the steps of:

determining a purity of a reagent associated with at least one of the reagent resources comprising an estimation of a carry over volume of the reagent during a predetermined time interval of a tissue processing protocol;

assigning the reagent for use in a predetermined tissue processing protocol step in accordance with the determined purity of the reagent.

The present invention also encompasses a histological tissue processing apparatus operating in accordance with the method steps of any one of the above disclosed methods.

Specifically, in preferred embodiments, the present invention encompasses a histological tissue processing apparatus comprising two retorts selectively connected for fluid communication to at least one of a plurality of reagent resources by a valve mechanism, said apparatus further comprising:

processor means adapted to operate in accordance with a predetermined instruction set, said apparatus, in conjunction with said instruction set, being adapted to perform the method steps of any one of the above disclosed methods.

Furthermore the present invention provides a computer program product including:

a computer usable medium having computer readable program code and computer readable system code embodied on said medium for, any one of managing resources; determining availability of resources; selecting a resource, controlling resources, or accelerating tissue processing steps in a histological tissue processor, within a data processing system, said computer program product including:

computer readable code within said computer usable medium for:

performing the method steps of any one of the above disclosed methods

In essence, an aspect of the present invention stems from the realisation that, in providing more than one retort a minimal and non-commensurate increase in the quantity of resources required to satisfy the processing requirements of multiple retorts is achieved through the management of resources on the basis of a relationship between selected resource properties and the processing protocols to be run in one or more of the retorts of a tissue processor. This also enables an efficient scheduling of protocols for use in one or more retorts using only one set of shared resources with a minimal increase in quantity compared to the quantity of resources required for a single retort where protocols are scheduled to run without conflict or interruption. The present invention further provides for an increased throughput of tissue sample processing by way of a method of management and control, respectively, of thermal resources in which, inter alia, states of resources are updated and thermal power is allocated in accordance with the updated states and predetermined criteria and, control algorithms are applied to heaters based on a number and location of temperature sensors and a state of a tissue processor component.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Further disclosure, objects, advantages and aspects of the present invention will be readily apparent to one of ordinary skill in the art from the following written description of preferred embodiments taken in conjunction with the accompanying drawings, which are given by way of illustration only, and thus are not limiting to the scope of the present invention, and in which:

FIG. 9 shows a rear view of the tissue processor shown in FIG. 3.

DESCRIPTION OF PREFERRED EMBODIMENTS

Figure 1:
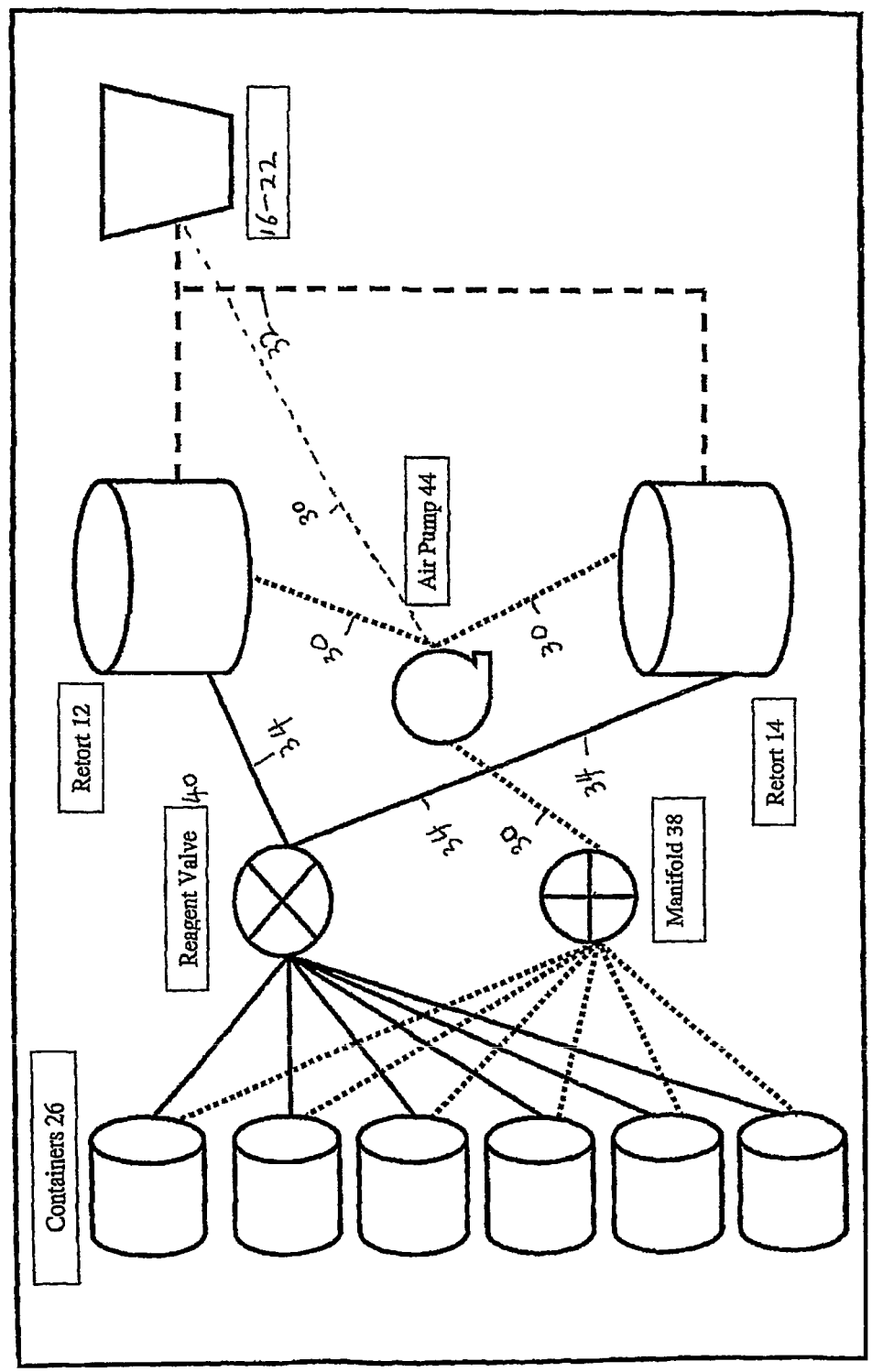
FIG. 1 is a simplified schematic block diagram of a tissue processor operating according to a first embodiment of the invention and showing the basic elements of a tissue processor.

The present invention has particular application in the operation of a tissue processor for processing tissue samples for histological analysis, such as that described in International PCT Application No. PCT/AU02/01337, publication No. WO 03/029845, titled; "Histological Tissue Specimen Treatment", published 10 Apr. 2003 and filed by the present applicant. In its preferred form, the present invention may be utilised as a method and means for managing resources and scheduling protocols in the operation of a tissue processor such as disclosed in WO 03/029845 and, it will be convenient to hereinafter describe the invention in relation to the tissue processor disclosed in that application. It should be appreciated, however, that embodiments of the present invention are not limited to that particular application, only.

The following detailed description of preferred embodiments of the present invention provide logical workflows, which in turn illustrate the functionality of an instrument, such as that described in WO 03/029845, operating in accordance with a preferred method of the present invention. Embodiments of such an instrument may have one rotary valve, two retorts, four wax chambers and a total of 22 valves. Furthermore, for example, the present invention has enabled a minimal number of shared reagent resources to be used, as in the preferred embodiments. As such, the instrument described in the preferred embodiments has 16 shared reagent stations between two retorts. This number is only three more reagent stations than required in the prior art for a single retort processor. Up to this point the management of resources dictated that up to 26 reagent stations may have been necessary to satisfy the requirements of two individual instruments operating with tissue processing protocols in a single retort each.

In the following description, device workflows that may be considered as lower level workflows, for example "fill" and "drain" retort, are actions that would be well understood by the person skilled in the art and the exact methodologies employed in carrying out these actions stem from the protocol scheduling disclosed herein. These are the basic actions that enable an instrument to carry out any higher level operation such as a protocol schedule. Instrument workflows may be higher level workflows that utilise some of the device workflows. Some examples of the higher level flows are cleaning protocols, wax cleaning, and remote drain. The workflows may be represented using basic unified modelling language flowcharts.

To assist the skilled addressee in understanding the present invention and its embodiments, the following terms are used throughout this description of the invention and its appended claims with the corresponding meaning set out as follows.

"Station": the term station indicates a resource point of supply. In a preferred embodiment the term refers to a reagent source and its attributes. This may be the actual reagent, its container, its status or a combination of one or more of these. For example, in a preferred embodiment of the invention where the instrument as disclosed in WO 03/029845 is utilised, the instrument has 20 stations comprising 16 reagent bottles and 4 wax chambers as noted above. Reagents may come from a variety of sources. Functional and to some extent physical similarity between the reagent bottles, wax chambers and an external bottle means that they can be grouped under one conceptual heading called a "station".

"Group": the term group relates to a resource's function. In a preferred embodiment the term refers to a reagent's chemical function. For example, a group may comprise those reagents that are dehydrants. In a preferred embodiment, eight fixed reagent groups are utilised by the system, namely, Fixatives, Dehydrants, Defatters, Clearers, Wax, Cleaning Solvent, Cleaning Alcohol and Cleaning Water.

"Type": the term type refers to attributes of a resource from a group. In a preferred embodiment, the term refers to a particular reagent within a group. For example, in a preferred embodiment when assigning a reagent type called "Ethanol 70%", this is a denomination for a particular reagent within the dehydrants group, namely, ethanol with a nominal concentration of 70%. It is to be noted, however, that a reagent "type" denomination does not affect the actual reagent concentration. The reagent concentration recorded by the system may default to the reagent's type concentration but is ultimately determined by the actual concentration management options set for the reagent concentration at each station. As an example, the reagent type selected at a station may be "Ethanol 80%", however, the reagent's actual concentration is the proportion of its major component, which may be 80% ethanol and 20% other substances comprising an initial diluting agent plus contaminants introduced by use.

In a preferred embodiment, each station is set to a reagent type and has a concentration, use history and a status. Each station is identified by its location. The system may automatically track and update station properties based on use. The same reagent type may be used in more than one station; however, actual or determined concentration, use history and status are unique to each station.

Where a computer processor device carries out a method in accordance with an embodiment of the present invention, wherever timers are taken to be used in the following description they may be implemented using an interrupt based timer, or preferably a system clock may be polled on initialising a timer and subsequently on each pass through a loop to determine whether the required time period has elapsed. Furthermore, as would be understood by the person skilled in the art, result codes may be used to define the success/failure status of a routine and the appropriate recovery action that is required, whereas error codes may be used to log the exact details of an error condition occurring for service troubleshooting purposes.

In this document the term vessel may mean either a single retort or wax bath.

The term "state" may indicate, inter alia, the fill-level of a station, a retort or a wax bath. The state of such a component may determine which actions are permissible in a protocol; for example, a "dry" retort may be filled with any reagent, while an "empty" retort may only be filled with a compatible reagent. Further, for reagent stations, the following states have the associated meanings.

"Full"; there is sufficient reagent available to fill a retort. In particular, this does not mean that a retort is necessarily filled to its volumetric capacity rather this term is intended to mean that there is sufficient reagent to fill a retort to a point that a tissue processing step may be performed with efficacy.

"Part Full"; the reagent level is between full and empty. Occurs usually during fill or drain.

"Empty"; the volume of reagent drained from the station is equal to the retort fill volume. There is still reagent in the station.

"Dry"; the volume of reagent drained from station is negligible in respect of processing a tissue specimen but is sufficient to contaminate a volume of reagent held by a station. Accordingly, some reagent residue remains at station.

"Unknown"; the container at station has been removed. Replacement is required and also reagent and state details may be prompted from user.

Description of Histological Tissue Processor

Figure 2:
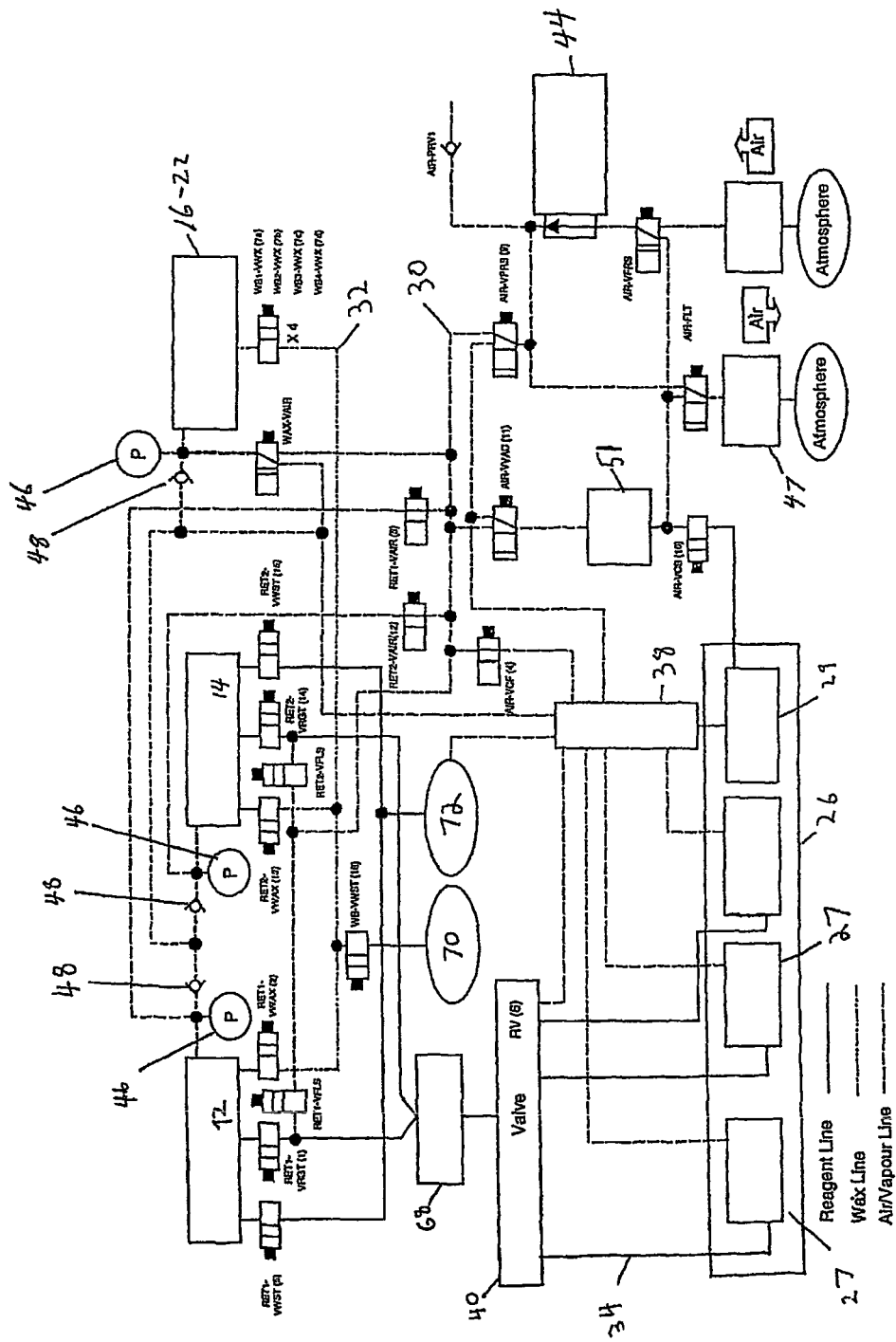
FIG. 2 is a more comprehensive schematic block diagram of a tissue processor of FIG. 1 showing air and reagent lines.

In FIG. 1 an example of a general schematic of the tissue processor 10 is shown, indicating major features such as retorts 12 and 14, four infiltrating baths 16-22, containers 26, reagent valve 40, manifold 38, and air pump 44. There are three main fluid sub-systems connecting the major elements, one sub-system being the air lines 30 from pump 44 to infiltrating baths 16-22 and retorts 12 and 14. A second sub-system being infiltrating lines 32 connects infiltrating baths 16-22 to the retorts 16-22. A third sub-system is reagent lines 34 connecting the containers 26 to the reagent valve 40 and the retorts 12 and 14. Valving as shown in FIG. 2 ensures that fluid flows along the lines to the correct destination, and FIG. 2 shows a specific embodiment of fluid line connection and valve placement relative to the aforementioned elements. The electrical connections between the controller 25, valves, pump 44 and other elements have been omitted from FIG. 2 for clarity, and are considered standard fittings. Also omitted from FIG. 2 are the numerous containers 26 and their respective connections to the reagent valve 40, to provide clarity. The omitted connections are identical to the connections shown in FIG. 2.

Figure 3:
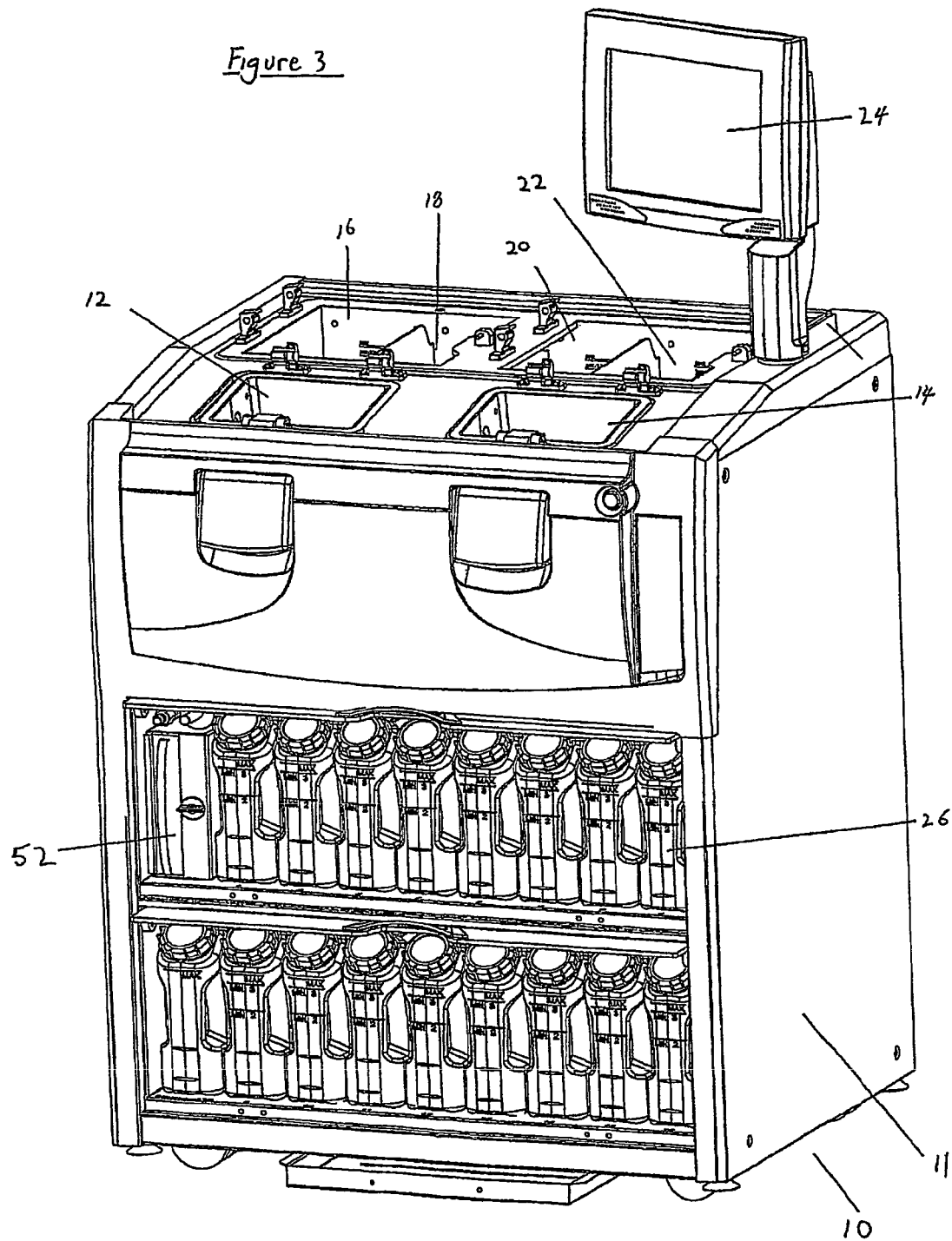
FIG. 3 shows a perspective view of an embodiment of the tissue processor of FIG. 1 and 2.

The schematic of FIG. 2 is embodied in the examples shown in FIGS. 3 and 9.

With reference to FIGS. 3 and 9, the tissue processor 10 includes control interface 24 that employs a graphical user interface to enable a user to operate the tissue processor 10 by controller 25. In the present embodiment the controller 25 is located in cabinet 11, however the interface 24 and controller 25 may be located separately, for example as part of a stand-alone personal computer. The controller 25 may include a personal computer processor such as a Celeron chip by Intel Corporation located on an ETX form factor PCB (not shown). The controller 25 may contain or store a number of predefined protocols (or steps) for processing tissue, the protocols being stored in a non-volatile memory such as a hard drive. Protocols may be programmable by the user to implement a number of steps for tissue processing, or they may be predefined. Typical protocol parameters include which reagents are to be applied to the samples, how long the reagents are to be applied, the temperature at which the reagents are applied, whether agitation is to take place, and whether ambient pressure in the retort is to be changed.

In FIG. 3, the retort 12 and 14 can be seen in front of infiltrating baths 1622. The lids for the retorts 12 and 14 have been removed for clarity, as have the lids for the infiltrating baths. In the present embodiment each retort 12 and 14 would have a lid (not shown), and each pair of infiltrating baths would also have a lid 17 and 19 (shown in figure g). The lids may seal with the retorts and baths when in a closed position.

The containers 26 may be located under the retorts 12 and 14 so as to be accessible to a user. The controller interface 24 in FIGS. 3 and 9 employs a touch screen, however other input and display devices may be employed. Also located under the retorts 12 and 14 is a filter unit 52, which typically includes a carbon filter to absorb vapours from air expelled from the processor 10.

In FIG. 9 the various fluid lines such as reagent lines 34 from reagent containers 26 can be seen attached to a reagent valve 40. The reagent valve 40 may have inputs from all containers 27, and a single output to retorts 12 and 14. A number of air lines can also be seen connecting manifold 38 to the reagent bottles 26. The connections between various elements in FIG. 9 are shown schematically in FIG. 2.

Figure 4:
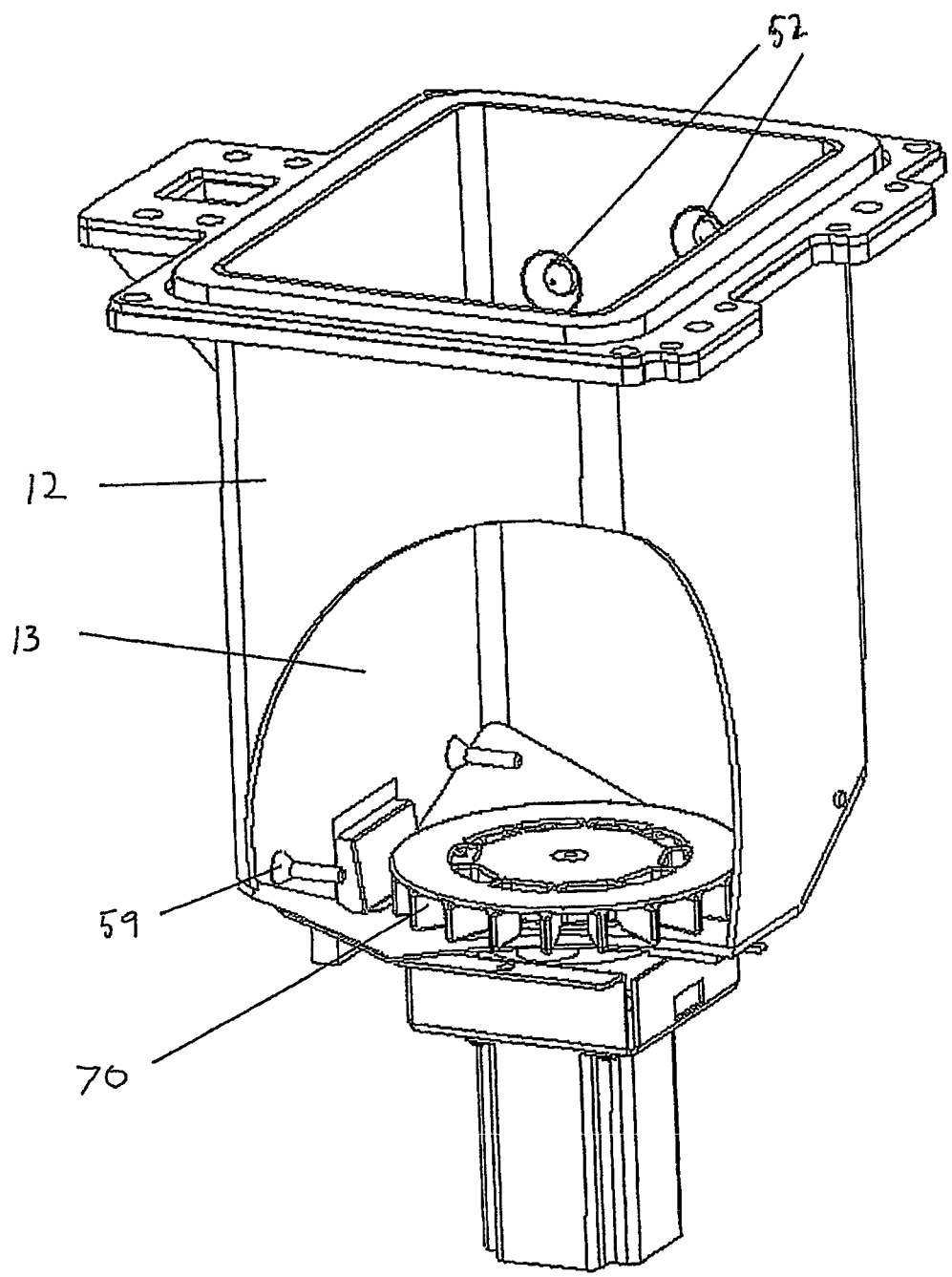
FIG. 4 shows a perspective cut-away view of a retort of the tissue processor shown in FIG. 3.
Figure 5:
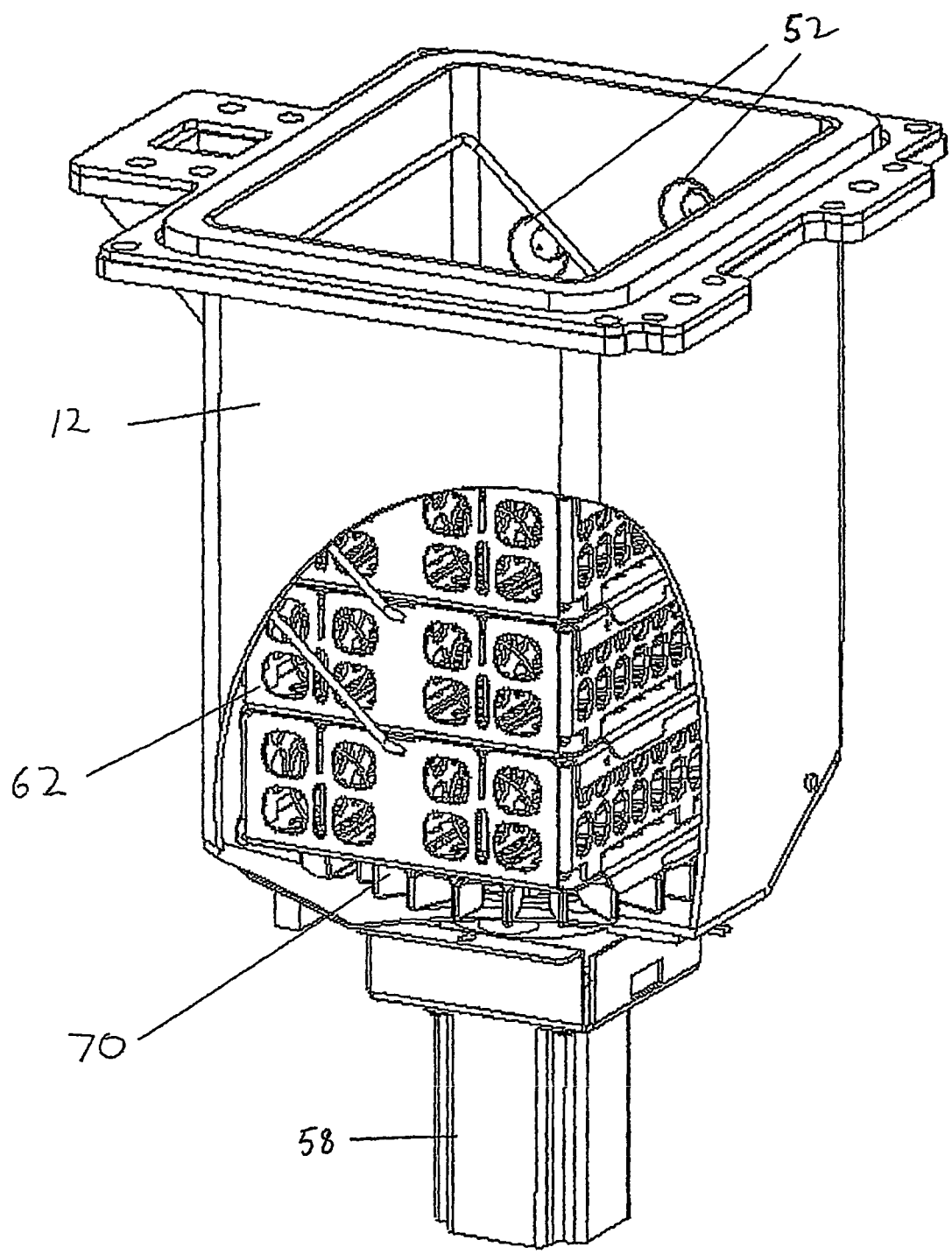
FIG. 5 shows a similar perspective cut-away view of the retort of FIG. 4 with cassette baskets in place.
Figure 6:
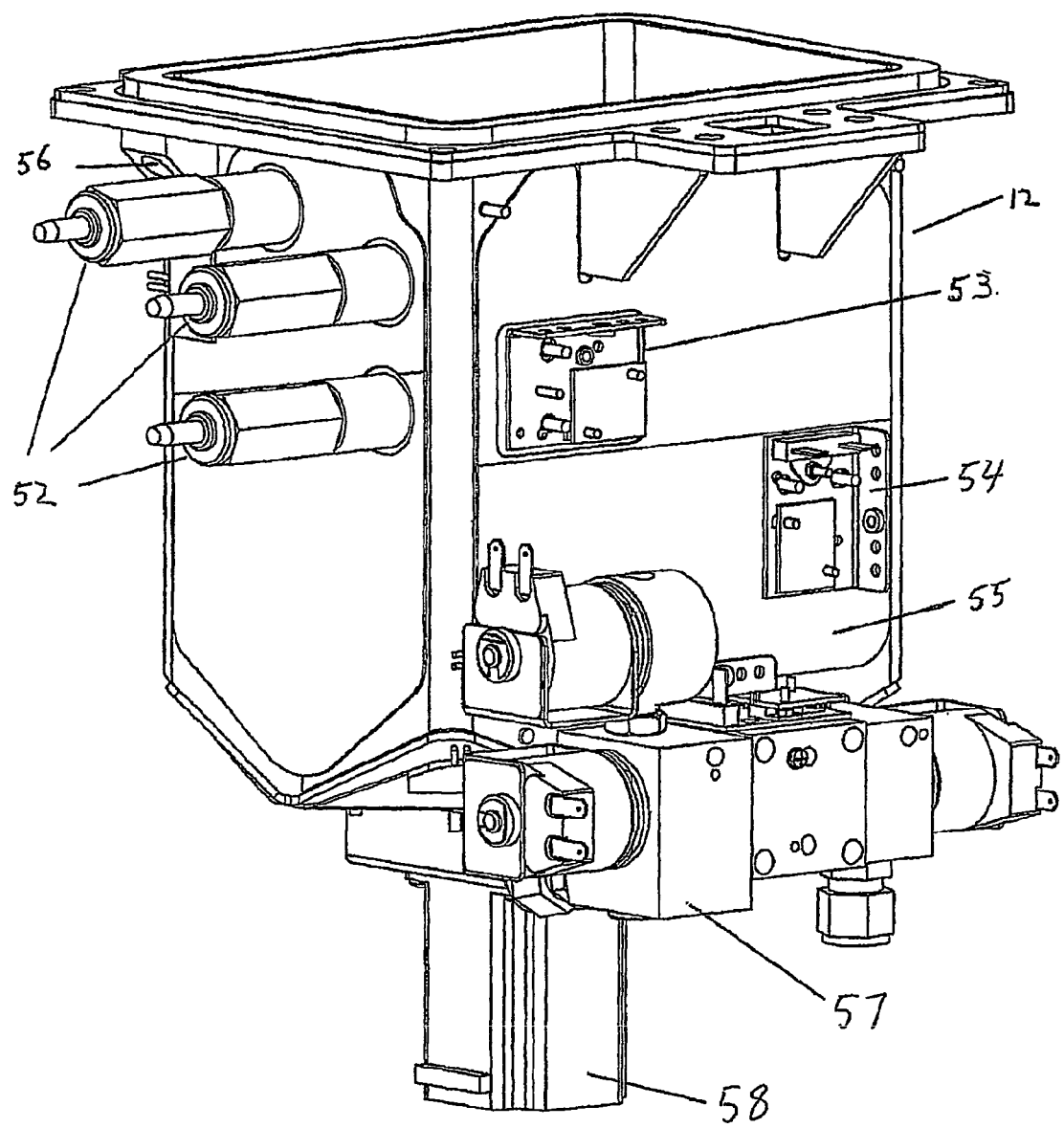
FIG. 6 shows a front view of the retort shown in FIG. 4.

One embodiment of retort 12 is shown in FIGS. 4-6, including a receptacle 13 for receiving baskets 62 containing tissue samples. The receptacle has a working capacity of 5.5 liters, however it may not necessarily be completely filled during each step of a protocol. When located in the processor, the retort may be rotated 10 degrees forward towards the front of the processor 10. This allows easier access to the baskets, as well as providing a drainage point, which is lowermost in the receptacle 13, minimising residuals remaining in the retort 12 after draining.

Sensors 52 are used to detect the level of fluid within the retort 12, so that the controller 25 can ascertain when to turn the pump 44 on or off, or open and close the appropriate valves, as described below. In FIG. 6, the placement of the three sensors 52 can be seen. The lowermost sensor detects when the level of liquid, for example reagent or infiltrating fluid, is above a minimum level. The minimum level may represent a partially filled receptacle, which is desirable when operating in economy mode. This is desirable when two or less baskets are to be processed at once, whereupon only approximately 3.8 liters of fluid are required to cover the baskets and samples contained therein. As the baskets may be various sizes, the level of the lowermost sensor and therefore fill volume for economy mode can vary in different embodiments of the retort 12. The middle sensor 52 detects when the level of liquid typically covers three baskets, which is a normal full load. The top sensor 52 detects an overfill situation. In this particular embodiment the sensors are optically based relying on a change in refractive index when liquid comes into contact with a prism (not shown) of the sensor. Each basket may hold approximately 100 samples either in individual cassettes or placed directly into the basket. Thus a full load for the embodiment of the retort 12 shown in FIGS. 4-6 is approximately 300 samples. The retorts may be made larger or smaller depending on requirements.

Also shown in FIG. 6 is temperature sensor 53, which is mounted directly to the retort 12, and temperature sensor 54, which is mounted to a heating mat 55. The retort 12 is heated to ensure correct reagent, or infiltrating fluid temperature. Placing a temperature sensor directly on the retort 12 allows the fluid temperature within to be measured more accurately than by measuring the temperature of the heating mat, especially where the fluid used may have low thermal conductivity. The temperature sensor 12 is substantially unaffected by the heating mat 55, directly. The temperature of the heating mat may then be kept at a maximum while the temperature of the retort 12 is below the maximum processing temperature or more precisely, the desired operating temperature of the retort, providing more rapid heating than if only one temperature sensor was employed. The methods employed to heat the retort are described in more detail below under the discussion of Thermal Resources.

With further reference to FIG. 6, Port 56 allows connection of an air line 30 to the retort 12. Retort manifold 57 also allows connection of infiltrating line 30 and reagent line 34 through a common entry point (not shown) at the bottom of the receptacle 13. In FIG. 2, retort manifold 57 incorporates valves ret1-vrgt and ret1-vwax, and is located at the front of the tissue processor 10 so that the lean angle of 10 degrees of the retort causes all fluid to drain towards the common entry point.

In FIGS. 4 and 5, the interior of the receptacle 13 is shown, including agitator 70. Agitator 70 is magnetically coupled to an electric motor 58, and may be driven at a number of speeds dictated by controller 25. The baskets 62 each contain up to 100 tissue samples. The baskets 62 are supported clear of the agitator on posts 59 shown in FIG. 4.

In the present example, retort 12 and 14 are of identical construction, size and operation, however one retort may be larger or more volumnous than the other. Connections to and from retort 12 are duplicated on retort 14.

In FIG. 2, pressure relief valves 48 are shown in fluid communication with air lines 30, retorts 12 and 14, and the infiltrating baths. Any overpressure in these lines will result in excess air being vented to waste through the manifold and filter 47.

A list of valve functions is as follows with reference to FIG. 2:

Valves ret1-vwst and ret2-vwst connects retorts 12 and 14 to waste container 72, when a waste cycle is required. Only one retort will be emptied at once and therefore these valves only open one at a time. In another embodiment, the valves ret1-vwst and ret2-vwst may be omitted, and waste container 72 may be directly connected to the reagent valve 40. To drain a reagent to waste, the reagent valve 40 connects to the reagent line 34 connected to the waste container 72, and the valve on the retort is opened to drain reagent directly to the waste container 72.

Valves ret1-vrgt and ret2-vrgt allow reagent flow into and out of their respective retorts during filling and draining of the retort. When draining a retort, these valves are open so that reagent may flow back down the reagent line and back into the same reagent container 26 from whence it came. It can be seen that air valves ret1-vfls and ret2vfls connect to the reagent lines 34 below the ret1 vrgt and ret2-vrgt valves. These air valves are used to purge excess reagent from the reagent lines after filling one retort. This is desirable as using reduced pressure to draw fluid into a retort reduces fluid pressure along the whole reagent line 34, and therefore when pressure is restored to the reagent line 34 some reagent may travel up the line of the retort that was not filled. Opening these valves, or opening the valves and pumping air down the air lines into the reagent lines clears excess reagent, preventing or reducing cross contamination.

Valves ret1-vwax and ret2-vwax connect the retorts to the infiltrating baths, via infiltrating lines 32 and valves wb1-vwx to wb4-vwx. Valves ret1-vwax opens when infiltrating fluid is to enter or drain from retort 12, and wb1-vwx to wb4-vwx open one at a time depending on where the infiltrating fluid is being sourced. The infiltrating line 32 between the infiltrating baths and retorts is heated to ensure that the infiltrating material does not harden in the lines.

Valves ret1-vair and ret2-vair are used to control air from the air pump to the retorts. Air may be supplied either at a positive pressure to ambient, or withdrawn from the retorts so that pressure inside one or both retorts is below ambient pressure. These valves determine which retort is in fluid connection with the air pump. Also air-vprs must be open to allow communication between the pump and the valves, otherwise air is directed toward wax-air valve, connected to the infiltrating baths.

Figure 8A:
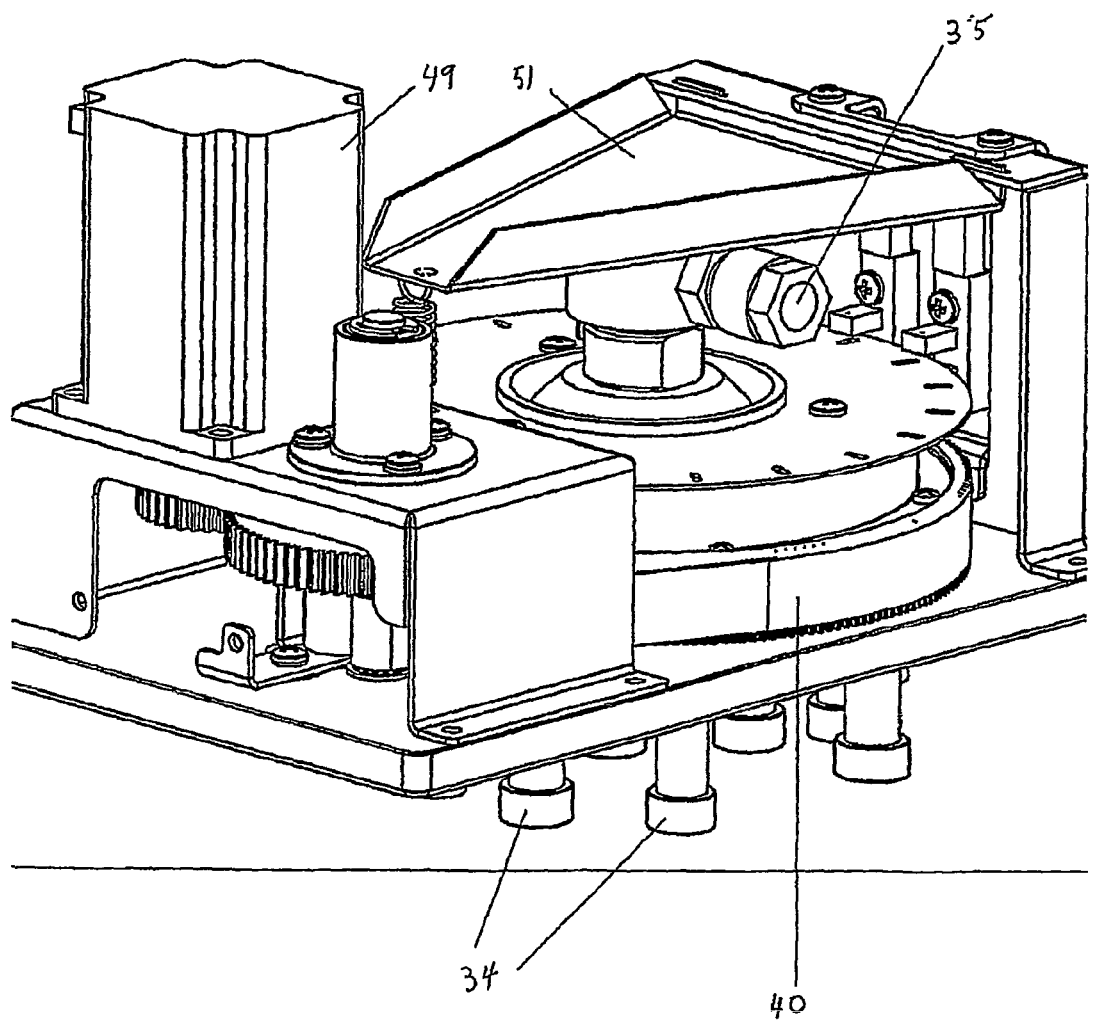
FIGS. 8a and 8b show views of an example of a reagent valve used in the tissue processor of FIGS. 1, 2 and 3.
Figure 8B:
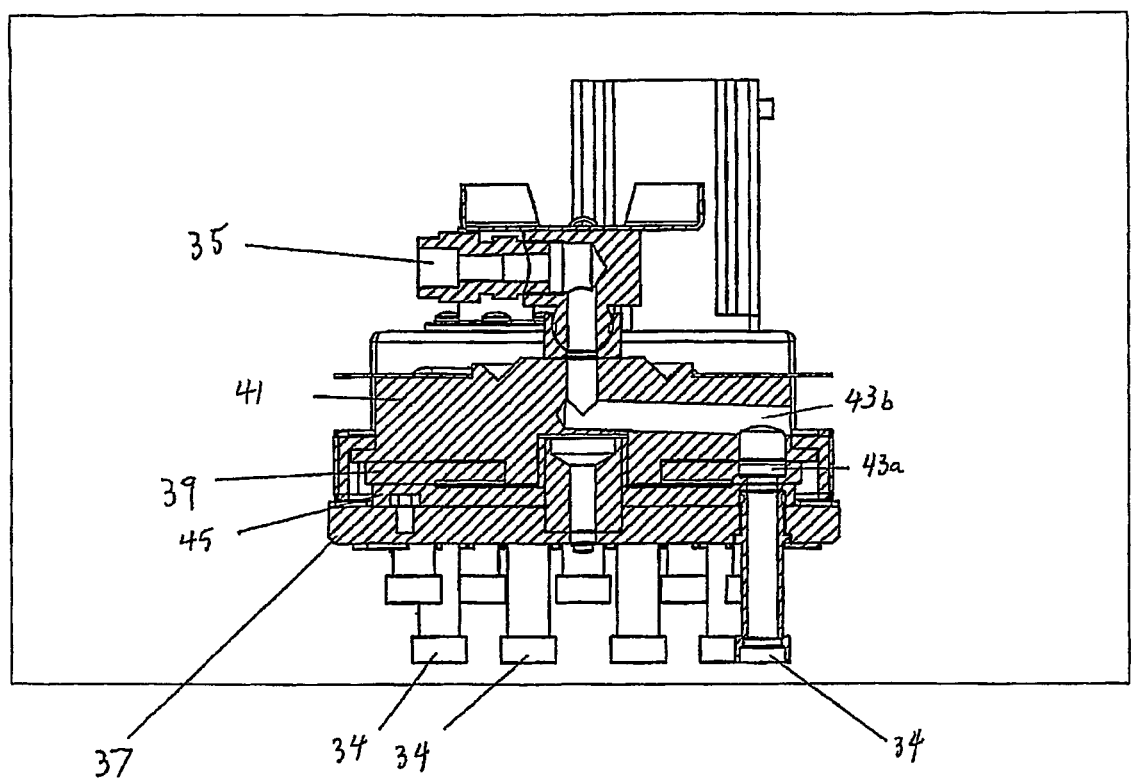

The reagent valve 40 is shown in FIGS. 8a and 8b, and includes connections between the reagent lines 34 from the reagent containers 26 on the input side, and outlet 35, which is fluidly connected to the retorts 12 and 14. The reagent valve 40 selects which reagent container will be in fluid communication with the reagent line connected to the retorts. In the present embodiment, the reagent lines 34 from the reagent containers 26 are arranged in a circle attached to the reagent valve housing 37. In the present embodiment, the reagent valve 40 is in the form of a rotary valve, having two ceramic discs 39 and 41, disc 39 having a single aperture 43a aligned with aperture 43b to form a conduit for reagent. The discs are mounted coaxially and adjacent each other and rotate together according to the position dictated by the controller 25. Disc 45 has an aperture for each reagent line 34, although in FIG. 8b only one aperture is in the plane of the cross section. The rotating discs 39 and 41 rotate with respect to disc 45, driven by stepper motor 49 such that the apertures align to provide a flow path from the outlet 35 (and therefore one retort) to a reagent container 26. In order to assist with sealing between the discs 39, 41 and 45, a plate 51 applied pressure to the discs. In this way any reagent line 34 and therefore any reagent container can be selected by the controller 25 to be in fluid communication with one of the retorts 12 or 14. This type of valve has a small internal volume and therefore minimises cross contamination. Further, the reagents are drained back into the reagent containers after each step and therefore little reagent remains to contaminate the subsequent reagent. It should be noted that the infiltrating fluid does not pass through the reagent valve. This separation of fluid flows prevents the reagent valve from clogging and reduces the amount of cleaning of the valve.

In use, the tissue samples to be processed are typically placed into cassettes (not shown) for placement into a basket 62. Generally, tissue samples expected to have similar processing times and to be exposed to the same processing protocol are placed together in the same basket 62. The basket 62 containing the tissue samples is then placed into one of the retorts 12 or 14, and the lid closed, forming a sealed enclosure. An operator may then enter data into the control interface 24 to instruct the controller 25 of the protocol to be followed. The protocol may be programmed step by step, for example indicating the time, temperature, pressure, agitation and reagent for each step, or a pre-programmed protocol encompassing all steps may be selected.

The first step in a protocol, once the lid of the retort is secured, may be to fill the chosen retort (in this example retort 12 is chosen) with a fixing solution. A typical fixing solution is formalin, which may be held in one or more reagent containers. In order to fill the retort 12 with fixing solution, the pump 44 is switched on and valves open the air lines from the retort 12 to the inlet side of the pump, pumping air from the retort 12 chamber. The reagent valve is set to a position that fluidly connects the reagent line of the retort 12 to the specified reagent container for formalin. Other valves are opened along the reagent lines from the retort 12 to the reagent valve 40. The reduced pressure in the retort 12 is sufficient to draw fluid out of the reagent container, through the reagent valve into the reagent lines 34 and into the retort 12. The retort is heated by heater pads to a predetermined temperature selected and controlled by the controller. Sensors 53 and 54 may be used to control the temperature of the retort, and therefore the tissue and any reagent contained therein. One or more sensors 52 in the retort as shown in FIGS. 4 and 6, may be used to detect the reagent level. When the reagent level in the retort is sufficient, typically to cover the baskets 62 as seen in FIG. 5, the pump may be turned off or otherwise disengaged from the retort 12, for example by closing valve ret1-vrgt shown in FIG. 2.

After a length of time determined by the controller 25 (typically as programmed by the user), the reagent may be removed from the retort 12. This is accomplished by opening valve ret1-vair in the air line 30 and opening valve ret1-vrgt in the reagent line 34. Reagent will then drain from the retort 12 back into the reagent container from which it came, or back into a different reagent container, or to waste, according to the position of the reagent valve 40 determined by the programmed protocol. To assist in draining, the retort 12 may be positively pressurised by air from the pump 44, supplied along the air lines 30. In the present embodiment the reagent drains back to its originating container. If the reagent is contaminated, or has been used for the predetermined number of samples or washes, then it is drained to waste using a separate waste cycle.

During the retort filling with reagent from a reagent container, the air pumped from the retort 12 flows down an air line 30, some of which flows back though manifold 38 and into the reagent container, recirculating some of the air from the retort 12. Excess air pumped from the retort 12 will flow out through a condensing mechanism such as a condensing coil 51, and/or a carbon filter 47, both of which are designed to remove volatile organic or other compounds from the air before it reaches the atmosphere. The tissue processor 10 may have an outlet connection that allows the filtered air to be vented or further filtered by apparatus external to the tissue processor 10.

The second step in tissue processing may be the dehydration step. The methodology employed to draw dehydrating reagent into the retort 12 may be the same as described above, as the dehydrating reagent will be stored in a reagent container 27. The dehydrating fluid may contain a fluid such as an alcohol, for example ethanol. The dehydrating fluid may also contain some water, either intentionally added, or, where the dehydrating fluid has been re-used, water removed from previous samples. There may be a number of steps of the protocol where dehydrating fluid is applied to the sample in the retort, and at each step a different dehydrating fluid may be used. For example, a fluid may be used that has less water than a previous fluid, to draw out more moisture from the sample at each wash. The dehydrating fluid may additionally or alternatively contain isopropanol. Later washes with isopropanol provide properties that may be advantageous, as will be described below. Further additives commonly used in tissue processor dehydration fluids may be used, as the present embodiments are intended to be compatible with known dehydration fluids.

On a final wash with dehydrating fluid, the fluid is drained completely from the retort. This is accomplished by opening valves from the air pump as well as pumping air into the reagent lines to clear the reagent. A vapour flush may be employed where the pump flushes fresh air into the retort to clear any vapour from the reagent, such as a dehydrating fluid. Significant vapour may be present as the dehydrating fluid may have high partial pressure at the retort operating temperature. After the dehydrating step, a drying step may be employed, where the retort is heated by the heating mats 55, while air is pumped through the chamber by the air lines 30. This removes excess dehydrating fluid. The drying step may take several minutes or more, and the retort may be heated to 85 degrees Celsius, depending on the dehydrating fluid chosen and the sensitivity of the tissue samples to heat.

Another step in tissue processing is infiltrating of the samples. This is typically accomplished by an infiltrating material such as a paraffin wax. The wax is held in the infiltrating baths 16-22, which are heated to the desired temperature above the waxes melting temperature, which is typically 54 degrees Celsius. Wax pellets are typically added to an infiltrating bath, which heats the pellets until they melt and achieve a suitable temperature. Alternatively, pre-molten wax may be added directly to the baths. The wax is held at the elevated temperature, typically 65 degrees Celsius, until required. The present embodiment shows four infiltrating baths, however there may be more or less depending on retort and infiltrating bath volume. The infiltrating lines 32 run from the infiltrating baths 16-22 to both retorts 12 and 14, and include valves such as ret1-vwax and ret2-vwax, that allow one, some, or all baths to be fluidly connected to one of the retorts. The arrangement of the baths, valves, and infiltrating material lines enables samples in one retort to be washed with up to four different infiltrating materials. Further, the infiltrating material may be heated in one or more baths while the processor 10 is in operation and drawing infiltrating material from the remainder of the baths.

Figure 7:
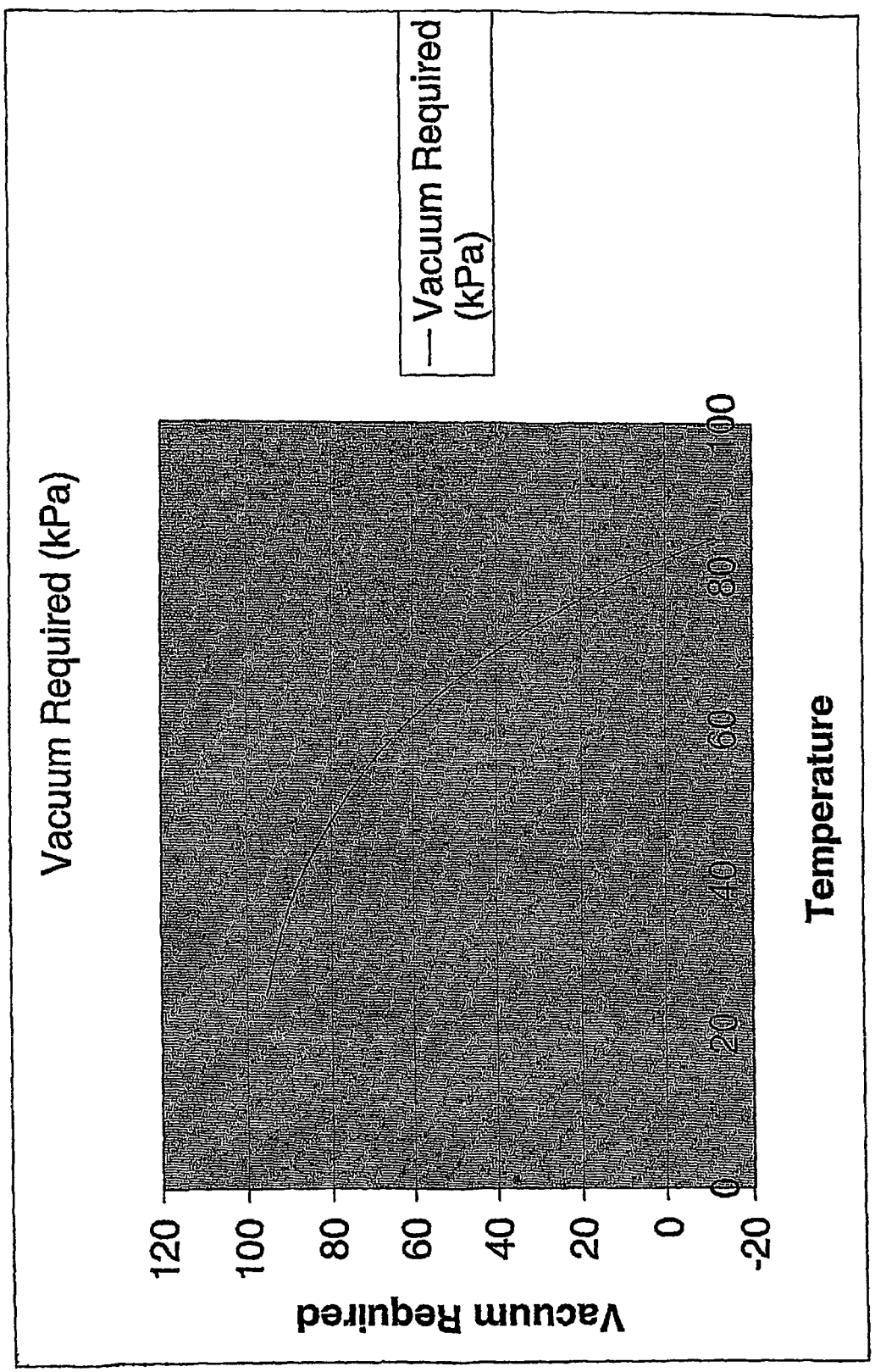
FIG. 7 shows a graph of isopropanol boiling temperature with respect to vacuum pressure.

During the infiltrating stage, the wax is drawn into the retort 12 by opening the valve between the retort and appropriate infiltrating bath, such as ret1-vfls, then reducing the pressure in the retort using the pump 44 and opening valves air-vprs and ret1-vair. The reduced pressure in the retort draws the wax into the retort 12. Typically the pressure may be −20 to −80 kpa gauge, however a wide variety of pressures may be used, and these are user programmable via the controller. The wax may be heated to a temperature above or approximately the same as the boiling temperature of the dehydrating fluid used in the last or last few washes. If an isopropanol is used, the boiling temperature will be approximately 82 degrees Celsius at atmospheric pressure. Ethanol typically boils at 78 degrees Celsius. After the retort has been drained of dehydrating fluid, some fluid remains on or absorbed by the tissue samples. The tissue samples may then be subjected to a drying stage as described above to remove further dehydrating fluid, and the retort flushed with clean air. Wax is then drawn into the retort. Upon contact with the heated wax, the remaining dehydrating fluid is evaporated or boiled off the tissue samples, and the wax replaces the dehydrating fluid, thus infiltrating the samples. The pump may continue to draw off air or vapour from the retort to reduce the pressure in the retort, which will reduce the evaporation temperature of the dehydration fluid. As an example, the pressure in the retort may be reduced by 50 kpa gauge, resulting in a boiling temperature of approximately 52 degrees Celsius for the isopropanol. A graph of boiling temperature compared to vacuum pressure is shown in FIG. 7. Reducing temperatures of the wax contacting the tissue samples may provide an advantage, for example where certain types of tissues do not perform well when exposed to high temperatures. Typically the paraffin wax used (Paraplast+ from Oxford Laboratories) melts at about 54 degrees Celsius. Other infiltrating materials may be used including resins used in histological processes for infiltrating tissue samples. In the present example the alcohol used at the last stage, isopropanol is not substantially miscible with paraffin wax. The means that infiltrating fluid is unlikely to penetrate the tissue sample if the previous fluid in the retort was immiscible with the infiltrating fluid. Boiling the volatile dehydrating material off therefore enables the omission of a step whereby an intermediary fluid such as xylene, which is miscible in alcohol and paraffin wax, is required. Xylene has undesirable properties in a laboratory. However, xylene will also evaporate when exposed to temperatures around 80 degrees, especially when applying a vacuum as described herein has lowered the pressure inside the retort. Thus the present example enables the tissue samples to be used without a xylene wash cycle, but also may be used with fluids such as xylene. There are advantages in not using xylene, including that xylene is miscible in wax, and therefore can be absorbed into the wax as a contaminant. However in some instances it is desirable to use xylene, for example when the tissue requires clearing and the dehydrating fluid such as isopropanol is deemed to be insufficient. Further, xylene may be used after a tissue processing cycle to clean excess wax from the retort, and therefore xylene may be present in the tissue processor.

It is possible to clean the infiltrating fluid of some of the volatile contaminants, such as the dehydrating fluid, clearing fluids such as xylene, by holding the wax in the bath and reducing the pressure in the bath. This clean cycle is done with the bath lid closed, whereupon the reduced pressure and holding the infiltrating material at an elevated temperature such as between 60 degrees and 100 degrees Celsius. In one embodiment the temperature may be held between 65 degrees and 85 degrees Celsius. By volatile material, it is meant that at the temperatures mentioned herein, and/or at reduced pressures, the material will boil or evaporate.

The vapour pressure of the dehydration fluid within the air in the container may also be reduced, for example by venting the air in the retort, either while maintaining a low pressure or cycling through pressure ranges. The infiltrating fluid may be held in the bath at an elevated temperature for several hours to clean away contaminants.

The use of two retorts allows two sets of baskets to be processed either simultaneously or with an overlap. Thus one retort can be loaded and a protocol begun while the other retort is mid-way through the same or a different protocol. This provides additional flexibility in the processor.

The tissue samples referred to in may be human or animal tissue samples, or samples from plant material.

An example protocol for tissue samples, such as a 3 mm punch human biopsy sample, will now be described:

| Step | Reagent | Time (min) | Temp (c.) | Retort Pressure | Agitation |
|---|---|---|---|---|---|
| 1 | Formalin | 5 | 60 | ambient | yes |
| 2 | 50/50 ethanol water | 25 | 60 | ambient | yes |
| 3 | 80/20 ethanol water | 35 | 60 | ambient | yes |
| 4 | Isopropanol | 30 | 60 | ambient | yes |
| 5 | Paraffin Wax | 40 | 85 | Vacuum | yes |
| 6 | Paraffin Wax | 5 | 85 | Vacuum | yes |
| | total time | 140 | | | |

Another protocol is as follows

| Step | Reagent | Time (min) | Temp (c.) | Retort Pressure | Agitation |
|---|---|---|---|---|---|
| 1 | formalin | 60 | 40 | ambient | yes |
| 2 | 80% ethanol | 45 | 40 | ambient | yes |
| 3 | 90% ethanol | 45 | 40 | ambient | yes |
| 4 | 100% ethanol | 60 | 40 | ambient | yes |
| 5 | 100% ethanol | 60 | 40 | ambient | yes |
| 6 | 100% ethanol | 60 | 40 | ambient | yes |
| 7 | 100% ethanol | 60 | 40 | ambient | yes |
| 8 | Isopar or d-limonene | 60 | 40 | ambient | yes |
| 9 | Isopar or d-limonene | 75 | 40 | ambient | yes |
| 10 | Isopar or d-limonene | 75 | 40 | ambient | yes |
| 11 | Paraplast | 70 | 60 | Vacuum | yes |
| 12 | Paraplast | 60 | 60 | Vacuum | yes |
| 12 | Paraplast | 60 | 60 | Vacuum | yes |
| | total processing time | 790 | | | |

From the above it can be seen that xylene is not required in this protocol, and that the protocol has few steps, saving time.

In one embodiment a contamination detector 68 may be placed in the reagent line 34 to detect the presence of contaminants in the reagents.

To drain the retort 12, the pump may increase pressure in the retort 12 by pumping air along the same air lines 34 as used to draw reagent into the retort 12.

Waste reagent may be drained into a reagent container, or be expelled to waste port 72. Infiltrating fluid may also be drained from the retort 12 to waste 70 by this method, and similarly infiltrating fluid may be drained from the baths using positive pressure.

In the above examples the dehydrating fluid is immiscible with the infiltrating material. However, the above process offers advantages even if a clearing cycle is used, where the clearing fluid is miscible with the dehydrating fluid and the infiltrating material. Further, additives may be used to increase the clearing properties of the dehydrating material, as well as increasing the miscibility of the fluids in the dehydrating and infiltrating steps.

While raising the temperature of the infiltrating fluid above the boiling temperature of the dehydrating reagent (or clearing reagent) will result in faster removal of the reagent, reagent will still be removed at or around the boiling temperature provided the partial pressure in the retort is lower than the partial pressure of the reagent at the given temperature. This can be accomplished by reducing the pressure in the retort, then allowing some fresh into the retort. Bringing fresh air into the retort while removing air laden with vapour will reduce the partial pressure of reagent in the air in the retort thus promoting more evaporation of the reagent. If the reagent is miscible with the infiltrating fluid it may not be necessary to remove all the reagent to obtain infiltration. However, if the samples can withstand the temperature it is preferable to raise the temperature of the infiltrating fluid within the retort to a temperature above the boiling temperature of the reagent for the given pressure. A temperature about the boiling temperature of a reagent for a given pressure may be typically a few degrees, such as 5 degrees Celsius, of the boiling temperature.

Other dehydrating fluids are contemplated as being able to be used with the present apparatus, such as
methanol
butanol
ethylene glycol
propylene glycol
Industrial methylated spirits
Denatured alcohol (including alcohol denatured with kerosene, benzene or brucine)
Reagent grade alcohols
acetone
and combinations thereof, however the above list is merely representative and is not intended to encompass an exhaustive list of reagents useful in the tissue processor described herein.

Clearing reagents such as di-pentene, D-limonene, 1,1,1, trichloroethane, toluene, and dioxane are also contemplated, and again this list is meant to be indicative of the types of reagents that may be used, rather than am exhaustive list.

The reagents above, and other reagents suitable for histological processes such as dehydrating, clearing or a combination thereof, may be used in the present apparatus with the step of evaporating the reagent from the sample using heating of the infiltrating fluid, provided the reagents evaporate without leaving a residue. While reagents such as butanol have a boiling point of approximately 118 degrees Celsius at atmospheric pressure, the boiling point drops dramatically with a reduction in ambient pressure. While it is believed preferable to not heat most tissues above 85 degrees Celsius, some types of well fixed tissue will survive this temperature without damage, and therefore higher temperatures may be used, increasing the range of reagents useful in the abovementioned processes. Accordingly, the upper temperature, which may be used, is dependent on the tissue, and therefore in well fixed tissue, temperatures may exceed 100 degrees Celsius. Reducing pressure in the retort will assist in reducing temperatures in the retort by reducing the boiling point of reagents.

Infiltrating materials such as resins and other fluids used in histological tissue processing are also contemplated in the above examples, and the present invention is not intended to be limited to the application of infiltrating materials mentioned herein. It is also contemplated that infiltrating material may be a mixture of substances, such as mineral oils and paraffin wax.

Description of Histological Tissue Processor System Workflows, Resource Management, Scheduling Protocols, Thermal Systems Resource Management—Reagents/Stations In accordance with a preferred embodiment, a reagent management system that controls reagent use to achieve improved tissue processing results has two parts: concentration management and reagent selection. Both parts utilise the improved method of managing resources disclosed herein.

Concentration Management (Purity)

Reagent concentration at each station may be used to select reagent stations for protocol steps in accordance with a reagent selection methodology, described in further detail below under Reagent Selection. Three options may be utilised for reagent concentration management; by calculation; by cycles; and by position.

Managing reagent stations using the calculation option is used in a preferred embodiment to produce improved tissue processing results. All factors affecting concentration are considered. An initial station concentration, which may be set to the reagent's default value, is used. Station use is then tracked to calculate current concentration. To calculate this, reagent carry over from the retort walls, baskets, cassettes and biopsy pads is used. In a preferred embodiment, reagent carry over volume is estimated from one or more of a) the number of cassettes based on a carry over volume per cassette and; b) the number of biopsy pads based on a carry over volume per biopsy pad. Preferably, the carry over per component is multiplied by the number of respective components to arrive at the estimate of carry over volume. Compatibility of each regent group may be considered and so the following components are tracked: water; fixative; dehydrants; clearant and wax.

The calculation may be applied during a predetermined time interval of a tissue processing protocol. The calculated concentration is preferably updated after each retort drain. The calculation is based on the number of baskets, cassettes, and biopsy pads processed and also allows for the receding reagent. It is assumed that there is no reagent carry over from a dry retort.

For each protocol step;

The retort fill level determines the number of baskets; the number of cassettes is either a default or a user entered number; the number of biopsy pads processed is determined by the cassette to biopsy ratio.

The reagent concentration may always be calculated but this calculation may be ignored when the "by position" or "by cycles" modes are selected.

Determining concentration by cycles uses the number of cycles each station has completed to determine the concentration ranking of each reagent within a group or type. A cycle is defined as a retort fill and drain. It has been found that the number of cycles often correlates to the degree of reagent contamination. However, this option may not allow for the number of cassettes and biopsies processed during a cycle or the interaction with preceding reagents.

Determining concentration by "position" uses station position or location to determine concentration ranking within a group or type. In a preferred embodiment, the concentration increases with station number.

Reagent Selection

The reagent management system selects the most appropriate reagent for each protocol step based on reagent station concentration. The reagent selection methods determine the selection of reagent stations for each protocol step. In accordance with the underlying method of managing resources disclosed herein, there are three selection methodologies; by group, by type, by station. A selection methodology is determined which may best suit processing needs and reagent management strategy.

Selecting Reagents by Group

Under group select methods, the system automatically selects between all reagents in a particular group to decide the most appropriate station to use in each protocol step. Stations may be assigned or allocated according to reagent group and concentration only. In other words, the selection may be exclusive of type. The station selection may also depend on the concentration calculation method used.

A group selection method may operate according to the following:

The station with the lowest available concentration is assigned to the first step in a protocol for each particular group.

The station with the highest available concentration is assigned to the last step in a protocol for each particular group.

Stations are assigned to intermediate steps such that the concentration increases at each step.

Where a protocol has a single step for a particular reagent group, the station with the highest available concentration is assigned.

The two highest concentration stations are reserved if possible. These reserved stations may be used in the last step of a particular group for protocols running in retort A and retort B.

Dehydrants used after a defatting step will not be assigned to the first two dehydrants steps unless the steps occur immediately after a defatting step.

Group selection provides the largest possible number of reagents from which to select. This is advantageous as reagent concentrations can be better balanced. Group selection protocols do not have fixed station assignments thus scheduling conflicts are minimized and the instrument may have steps reassigned when a station's state changes unexpectedly with other stations of the same group available.

Protocols with defatting steps are not as suitable for group selection as the highest concentration dehydrants are assigned to post-defatting steps. this may rapidly degrade the highest concentration or purest reagents and also make them unavailable for the first two steps of subsequent protocols. The type selection method described below, is more suited to defatting protocols, and as such a "post defatting dehydrants" type may be used.

Selecting Reagents by Type

When scheduling protocols using a type selection methodology, a selection between all reagents of a particular type is made to determine the most appropriate station to use for each step. Suitable reagents are identified by their type name and then stations are assigned according to reagent concentration. Here again, the reagent concentration is dependent on the concentration method selected.

The type selection methodology assigns available reagent stations to protocol steps according to:

The station with the lowest concentration is assigned to the first step for each particular type.

The station with the highest concentration is assigned to the last step for each particular type.

Stations are assigned to intermediate steps such that the concentration increases at each step.

Where a protocol has a single step for a particular reagent type, the station with the highest concentration is assigned to that step.

The two highest concentration stations are reserved if possible. These are reserved for the last step of a particular type for protocols running in retort A and retort 13.

Dehydrants used after a defatting step are not assigned to the first two steps for a particular type unless the steps occur immediately after a defatting step. This may apply by group as well.

The type selection method is preferred over the group selection where it is required that a protocol uses a particular type of reagent for a particular step or sequence. Type selection allows management of reagent use but not with as much flexibility as the group selection method. Type select protocols do not have fixed station assignments so scheduling conflicts are reduced and the system may reassign steps when a station's state changes unexpectedly and other stations of the same type are available.

Selecting Reagents by Station

This methodology may be chosen where complete control of reagent use is required and no reagent assignment flexibility is desired. The station specified is used only. In other words, the most appropriate station may not be selected, certainly not automatically. As reagents degrade, either protocols or reagent stations may need to be altered to ensure reagents with suitable concentrations are used. The station select method does not allow any instrument flexibility when scheduling protocols and may not allow for recovery from a processing error caused by unexpected reagent unavailability.

Replace Reagent

The purpose of the Replace Reagent workflow is to detect a change of reagent and request the user to update reagent properties.

A User Response Timeout is configured. It is nominally 120 s but may be configured. This User Response Timeout is the time before the instrument will assume there is no user present and clear the replace reagent screen Procedure At a frequency of once every 5 seconds the Bottle Replaced Flag is queried and the following is performed:

Sound an internal alarm for user attention

Display a screen informing the user about bottle that has been replaced

If the user updates invoke the Update Reagent (see below) Window to set the station details If the user does not respond within the timeout period close the window and do not change reagent status.

Update Reagent

The purpose of the Update Reagent workflow is to walk the user through updated properties of a reagent as a result of a user request or from replace reagent.

Required Inputs

Station being updated.

The following result codes are possible

| Result Code | Meaning |
| --- | --- |
| 0 - Successful - Station reagent details updated | Reagent details successfully updated |
| 1 - Failed - aborted by user | Reagent details unchanged |

Procedure

Request the following information from the user:
  Confirmation that the user wishes to change the reagent in the given station
  Reagent group and Reagent type
  Station purity
  Station Status Reset the age properties of the station.

Track Reagent Purity

The purpose of the Track Reagent Purity workflow is to continuously monitor reagent concentration or purity and calculate its purity level based on the number of runs and preceding bottle purity. Other properties, such as type of contamination are maintained. This should be done on a step by step basis as the reagent containers or bottles are returned from a retort Required Inputs Concentration and content of the bottles Cassettes in retort Proportion in the preceding bottle of the following components:
  Water
  Fixing agent
  Dehydrating agent
  Clearing agent
  Wax Configuration values

| Identifier | Default value | Meaning |
| --- | --- | --- |
| DefaultCassettesPerRun | 150 | To be used in Cassettes in Retort is intended to use the default |

-continued

| Identifier | Default value | Meaning |
|---|---|---|
| DefaultBiopsyPadPerCassette | 0.263 | Estimated number of Biopsy Pads expected to be present per cassette. Used to work out number of biopsy pads |
| CarryOverPerBasket | 17.08 | Estimated millilitres of carry over per basket |
| CarryOverPerCassette | 0.1 | Estimated millilitres of carry over per cassette |
| CarryOverPerBiopsyPad | 2.07 | Estimated millilitres of carry over per biopsy pad |
| CarryOverPerRetort | 5 | Estimated millilitres of carry over for an empty retort |
| BottleFillLevel | 3BasketLevel | The level to fill the bottle to. This may differ from the retort fill level of 2 or 3 basket. |

The following should be noted.
Purity is an attribute that is to be stored for both stations and retorts
Volume is an attribute of a station only
During manual operations the default number of cassettes is used
If entry of cassette numbers is used the default number of cassettes may be used
The number of biopsy pads is a proportion of the number of cassettes
Initial volume should be based on the BottleFillLevel (5 liter for 3BasketLevel, 3.8 liter for 2BasketLevel)
Five components shall be tracked
Water
Fixing agent
Dehydrating agent
Clearing agent
Wax.
If reagent management is turned off the purest bottles are the ones with the highest station number. Purity tracking may still be applied but purity used for station selection will be based on bottle position.
If reagent purity is tracking by cycle the purest bottles are those that have processed the least number of cycles.
Procedure
When the protocol is first started, estimate the carry over volume as follows:

$$Vco=(Nb \times Cb)+(Nc \times Cc)+(Np \times Nc \times Cp)+Vcr$$

Vco Volume of carry over (ml)
Nb Number of Baskets per Retort
Cb Carry over per Basket (ml)
Nc Number of Cassettes
Cc Carry over per Cassette (ml)
Np Number of Biopsy Pads per Cassette
Cp Carry over per Biopsy Pad (ml)
Vcr Carry over for an empty retort (ml)
The bottle volume (Vb) will be based on the bottle fill level. For a three basket bottle fill level the bottle volume used shall be 5 liters. For a two basket bottle fill level the volume used shall be 3.8 liters
After each fill, estimate the carryover amount in the bottle for each component using the following formula:

$$Vpc=(Pp \times Vco)/1000$$

Vpc Volume of a component carried over from previous bottle
Pp Proportion of component in previous bottle
After each fill estimate the volume of each component in the bottle:

$$Vaf=Vpc+(Vb \times Pbf)$$

Vaf Volume of component in the bottle after fill
Pbf Proportion of component in the bottle before fill
Vb Volume available in the bottle
After each fill estimate the proportion of each component in the bottle:

$$Paf=Vaf/Vb$$

Paf Proportion of component in the bottle after fill
After each fill present the purity of the nominated primary component as a percentage:
If the fill was a dehydrating group and the previous fill was a defatting group that station should be identified as not being available for as step as a graded alcohol or a step following a graded alcohol.
If a fill is for a cleaning reagent the number of baskets and cassettes should be assumed to be the default without any biopsy pads.
On a drain the proportion of components is allocated to the station.
After each drain (other than a drain during the Fill Bottles From Remote workflow) update the following parameters for the reagent station
Cycles
Number of cassettes
Days in instrument
If a station has passed outside its threshold values (and the threshold has not been disabled with Reagent Management) for purity, cycles, number of cassettes or, days in instrument then an error should be logged.
It has been found that the most significant values are Nc and Np because of their associated carry-over values Cc and Cp respectively and these may typically be as follows:
Cb=5 ml (default Nb=3=>15 ml)
Cc=0.25 ml (default Nc=150=>37.5 ml. max 75 ml for 300 cassettes)
Cp=2.6 ml (default Np=0.263=>102.57 ml for 150 cassettes. max 780 ml for 100% pads and 300 cassettes but this is not a common occurrence)
Vcr=5 ml
Select Station
The purpose of the Select Station workflow is to ensure uniform progression from reagent container to container or bottle to bottle as each step within a protocol proceeds.
Required Inputs
Information about the type of selection method (by group, reagent type or station)
Step information about the group, step in the group, reagent type, temperature, pressure and/or station selected
Passed Outputs
Station number of selected reagent Result Codes possible

| Result Code | Meaning |
| --- | --- |
| 0 - Successful - Step completed | Reagent was successfully selected |
| 1 - Failed - Unable to select reagent | Reagent Selection aborted, specified reagent was unable to be obtained |

A station is available at run time if the station is full, within purity/age thresholds, not in use in the other retort, is within specified reagent temperature tolerance and, in the case of a bottle, that the bottle is detected as within the instrument (unless overridden, for example, manually).

A station is available at schedule time if the station will be full at the time required by a protocol, within purity/age thresholds, is within the specified reagent temperature tolerance and, in the case of a bottle, that it is detected as within the instrument (unless overridden for example manually).

A station that is outside purity/age thresholds can be made available if there are insufficient reagents to allocate to the protocol otherwise.

Two "purest" available stations are put aside for each reagent group (if there are enough available stations to do so). These stations should only be used for the last step within a group.

The last step in a group (for select by group) should always try and use one of the "purest" stations.

The first step in a group (where there is more than one step in the group) should use the least pure available station.

If reagent management is switched off reagent purity shall be defined as the purest being the highest station number in a group as discussed above in relation to in Track Reagent Purity, namely, in one example, by position of reagent container or bottle.

If reagent management is switched to select by cycle the purest stations will be the ones that have recorded less cycles and the least pure stations will be the ones that have recorded the most cycles processed.

At schedule time no two steps in a row should use the same station allocation.

At run time the same reagent should not be allocated for more than two steps in a row.

Stations of the same group or type should always increase in purity according to ascending station number or position unless select by station is chosen.

Figure 10:
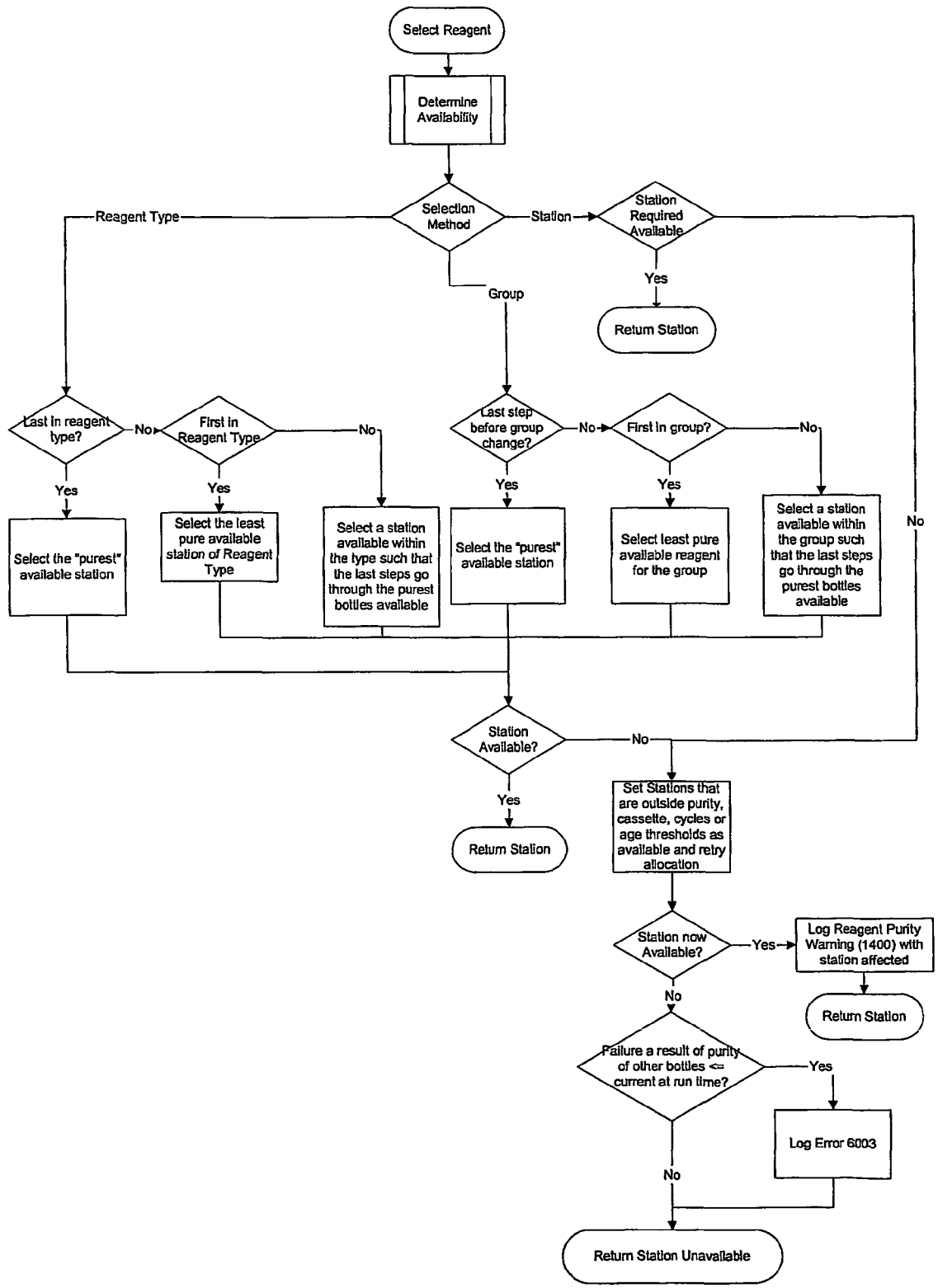
FIG. 10 is a flow chart of an exemplary workflow for selecting resources in accordance with a preferred embodiment of the invention.

An exemplary workflow for Selecting Reagent/Station is shown in the flow chart of FIG. 10. Availability of resources such as stations or reagents is determined first. A workflow for determining availability of these resources is exemplified by the workflow of FIG. 11. Upon determining availability a characteristic such as purity (concentration of reagent) is used to select the appropriate station according to the selection methodology being used, either by Reagent Group, Reagent Type or Reagent Station.

Station Availability

Figure 11:
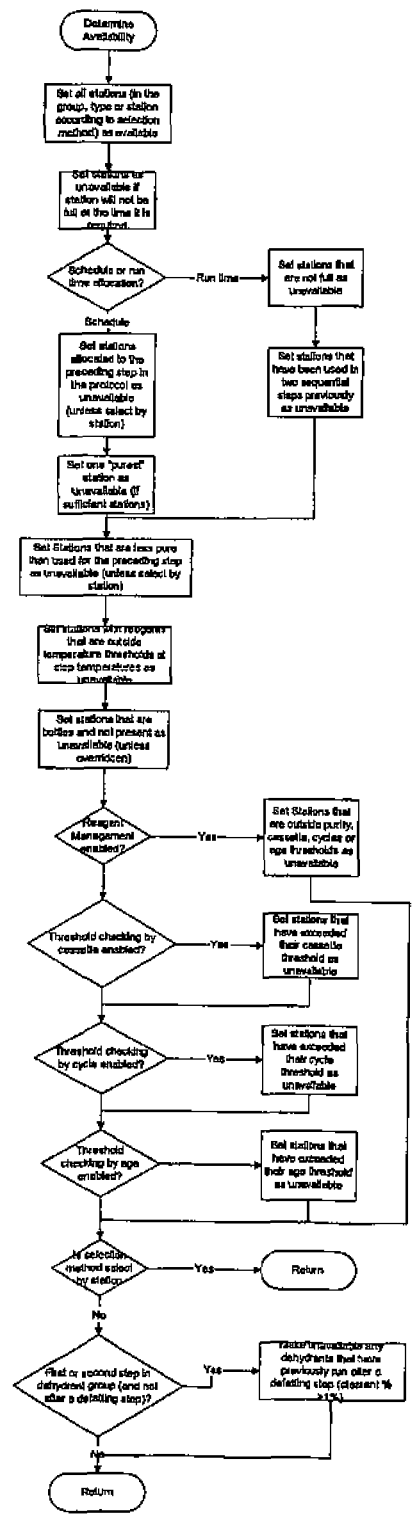
FIG. 11 is a flow chart of an exemplary workflow for determining the availability of resources in accordance with a preferred embodiment of the invention.

FIG. 11 is a flow chart of an exemplary workflow for determining availability of resources such as in this example, stations. In following the flow chart of FIG. 11, the following should be noted. Initially all stations whether using the Group, Type or Station selection method, are set as available. Then any stations that are not full at a time when they are required by a given protocol will be set as unavailable. It is possible that if a station is not full at the schedule time AND either in the other retort as part of a protocol OR in the subject protocol's retort AND compatible with the first protocol step, then that station may be set as available. In all other cases where the reagent container is empty the station should be set as unavailable.

Further in the workflow of FIG. 11, after setting one "purest" station as unavailable (if there are sufficient stations), the workflow then proceeds to set any further stations that are less pure than those used for the preceding protocol step as unavailable (unless select station is used as a selection method). Thus, when selecting by Group and Type, the workflow may not go back to a reagent used in a preceding protocol step for a given group or type except at run time, to the preceding reagent, if no more appropriate reagent is available. This same reagent may only be used in this way for no more than two steps in a row. A reagent may be used for an alcohol step following a defatting step.

Protocols

Run Protocol

The purpose of running a protocol is to perform a sequence of steps comprising applying reagents to tissue samples located in a retort at a specified "target" time, temperature, pressure and agitation to facilitate the processing of tissue.

Figure 12:
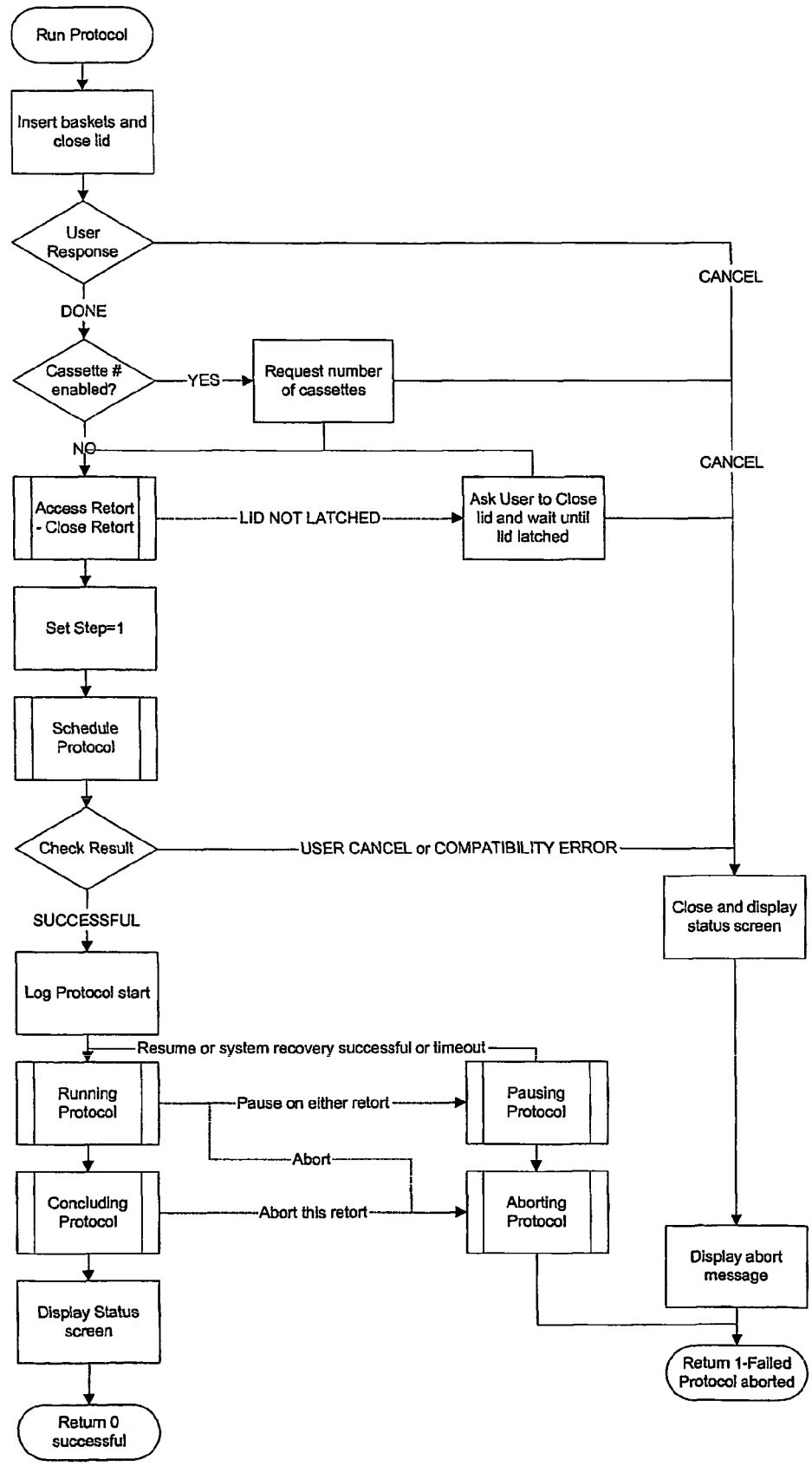
FIG. 12 is a flow chart of an exemplary workflow for running a single protocol suitable for application in the tissue processor of FIG. 3.

By way of background to the invention, an example workflow is shown in FIG. 12. The protocol outlined is for a single retort. With the exception of pause behaviour there should be minimal interaction between retorts. On error (requiring recovery action that impacts the scheduled completion time) the schedule for both retorts should be delayed unless the other retort has aborted. If the other retort has aborted the primary retort should reschedule, based on a single retort operating. A timeout may be utilised to this end. When a protocol has successfully completed this is notified and displayed to the user with an associated screen and audible alarms.

Required Inputs for Run Protocol

The inputs to the Run Protocol workflow are:
Run time Reagent Management information
Protocol details In configuring or reconfiguring the system a default pause time of, for example, 30 seconds may be used and will start counting down from before protocols recommence.

Upon running a protocol, two results are possible:

| Result Code | Meaning |
| --- | --- |
| 0 - Successful - Protocol completed | Protocol was successfully completed |
| 1 - Failed - Protocol aborted | Protocol aborted - user should be warned to take remedial action to recover tissue and prepare retort for processing. |

The following Behaviour and Error Codes apply to the Run Protocol workflow and its subflows, for a single protocol.

| Subflow | Error Code | Type of behaviour | Comment |
| --- | --- | --- | --- |
| Schedule protocol | 1 - Failed - Target Time unable to be met | Warn user and prompt for new target time | The user should be present during scheduling and therefore can be notified. The causes of this schedule error are the target time being unable to be met. |

-continued

| Subflow | Error Code | Type of behaviour | Comment |
|---|---|---|---|
| Schedule protocol | 4 - Failed - Abort | Abort the protocol | For this error to have occurred the user needs to have chosen not to confirm the schedule but wants to abort. |
| StartProtcolChecks | 6 - PrerequisiteCheckFailed, non overrideable | Abort protocol, raise an alarm and notify user | The user should be nearby the instrument having just accepted the schedule. |
| Change Reagent | 4 - Failed Abort | treat as "non fatal error condition" | This error should never happen, however, will be treated as a user recoverable error as outlined in the workflow |
| Access Retort | 6 - PrerequisiteCheckFailed, non overrideable | Abort the protocol where specified in the workflow | Should this error occur after the last step completes the protocol should be aborted. Recovery should occur using manual operations |
| Access Retort | 9 - Timeout | Abort the protocol where specified in the workflow | Should this error occur after the last step completes the protocol should be aborted. Recovery should occur using manual operations |
| Access Retort | 10 - Lid closure error | Prompt the user to close and latch the retort lid and retry | Handling for this may be detailed in a suitable access retort workflow. This error should only happen at the start of a protocol where the lid has not been latched |
| Access Retort | 11 - Access Retort Prohibited | Redisplay the request to drain | Handling for this may be detailed in a suitable access retort workflow |
| Access Retort | 12 - Drain Retort Error | Abort the protocol where specified in the workflow | Should this error occur after the last step completes the protocol should be aborted. Recovery should occur using manual operations |
| Access Retort | 13 - Vent Retort Error | Abort the protocol where specified in the workflow | Should this error occur after the last step completes the protocol should be aborted. Recovery should occur using manual operations. |
| Access Retort | 14 - Fill Retort Error | Raise a user alarm and display error message. Abort the protocol where specified in the workflow | Should this error occur the user should be alerted. This error occurs after a temporary access to a retort and the retort was unable to fill after access was completed |
| Access Retort | 15 - Lid Lock Error | An access retort routine has already raised a user alarm and displayed an error message. | Should this error occur the user will be alerted. Since this will only get to this level if the retort has failed to unlock the protocol can continue anyway. |

With particular reference to FIG. 12, the Run Protocol workflow is started. A user is requested to insert baskets and close the lid of a retort. The number of cassettes may be prompted from the user. After the appropriate actions from the user of inserting and recording the number of cassettes and closing the retort lid, the user is prompted to schedule a protocol as so desired at. This may include the user modifying or changing the end time for a protocol run, for example. Alternatively, the user may be prompted to select a new first step of a protocol by skipping initial steps. The user may also be prompted to set the priority of the retort. Upon scheduling, the system may then check the chosen settings of the user for compatibility with acceptable or legal scheduling options for tissue processing. After a successful result a loaded protocol is implemented and the sub flows of Running Protocol, Pausing Protocol, Concluding Protocol and Aborting Protocol may be actioned. A successfully concluded protocol is displayed for the user's notification and the workflow is completed with the successful result code returned. An aborted protocol either through the running of a protocol or preliminary cancellation at any of the indicated steps is also displayed for the user's notification and the workflow is completed with the failed result code returned. The person skilled in the art would appreciate appropriate sub flows may be utilised within the Run Protocol Workflow as shown in FIG. 10.

Schedule Protocol

Figure 13:
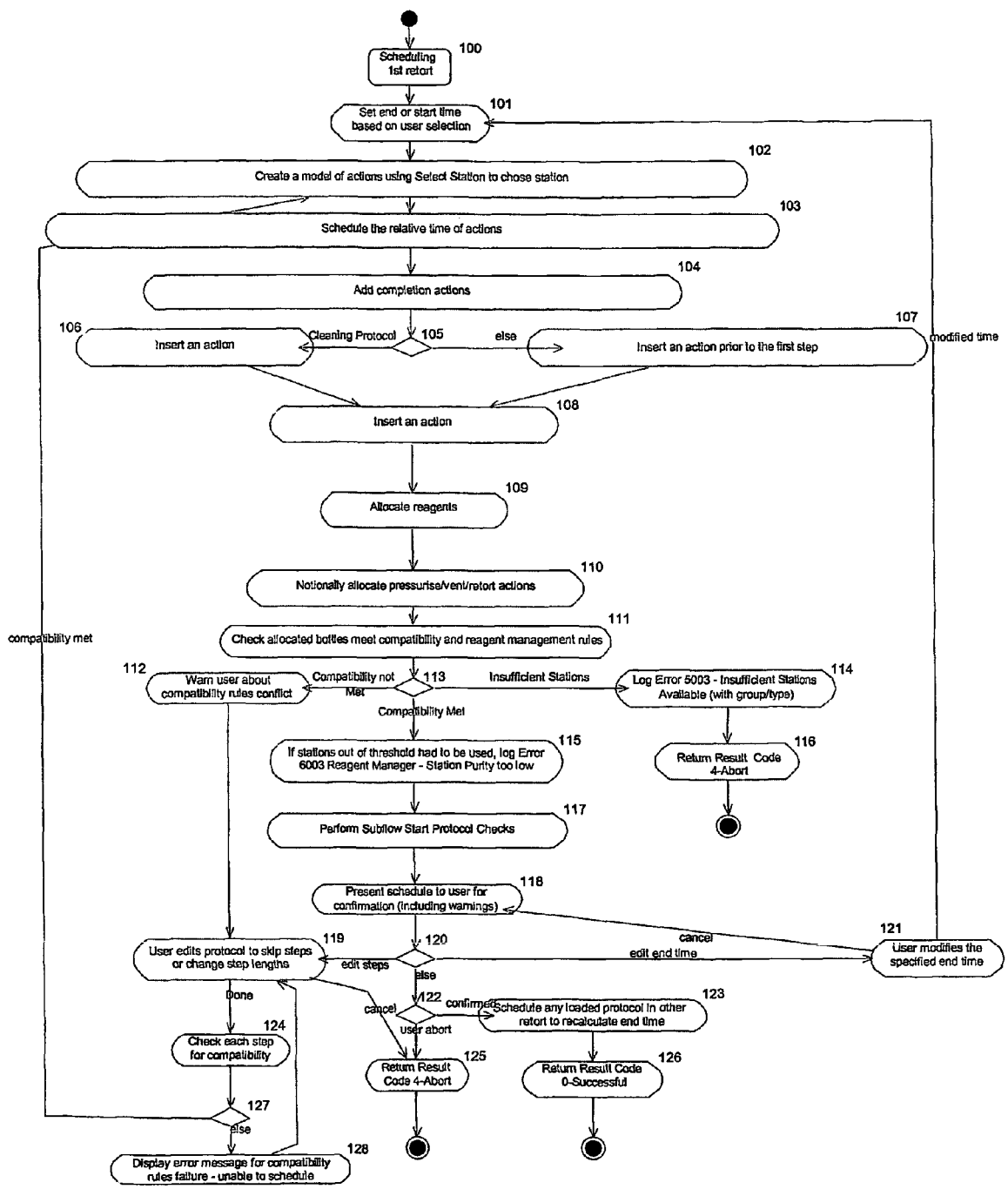
FIG. 13 is a flow chart of an exemplary workflow for scheduling a protocol suitable for application in the tissue processor of FIG. 3.

The purpose of scheduling a protocol is to obtain a time sequenced series of actions that avoids or minimises resource conflicts without affecting tissue quality. An exemplary workflow is shown in FIG. 13.

Required Inputs

The inputs to this workflow are:

Protocol to be scheduled

Reagent Management information

Passed Output

Actual start/end time obtained

Configuration values.

A WaxValveHeatTime of 300 seconds default is chosen. This is the time required for retort wax valves to heat to temperature and reach thermal equilibrium. All the timings may be taken to the level of atomic operations. Atomic operations being defined as those operations that cannot be broken down into further component steps.

The following Result Codes are possible

| Result Code | Meaning |
|---|---|
| 0 - Successful - Target time met | Schedule was successfully Completed |
| 1 - Failed - Target time unable to be met | Schedule failed - Warn user and prompt for new target time |
| 4 Failed - Abort | User did not accept the schedule |

With particular reference to FIG. 13, the user defines the boundary of a protocol by setting its end or a start time at 101. At 102 the user defines a model of protocol actions. These will have estimated durations. The individual action start times are relative to the specified start or end time of step 101. They may comprise fill, change reagent, retort manifold heat and retort heat. A station for each required reagent is chosen in accordance with the Select Station method described herein. At 103 the relative timing of the actions are scheduled taking account of step length, time of action and ensuring retort manifold is heated prior to the first wax step. WaxValveHeatTime workflow described herein is suitable for ensuring the effective heating of the retort manifold. If the first protocol step is a wax step, it should be ensured that the retort heaters are set to standby temperature at same time. The WaxValveHeatTime may include a delay time to bring the Retort Manifold to temperature if the first step is wax unless the manifold is heated and already at temperature. A last step to turn off the Retort Manifold heater on a final drain where temperature is ambient (eg. at the end of a cleaning protocol) may also be included. This leads to step 104 of FIG. 13 where completion actions are defined. The completion actions are to establish the concluding protocol conditions including turning off Retort and Retort Manifold heaters if specified temperature is ambient and draining the retort if this is specified. If a cleaning protocol is determined at step 105, an action is inserted at 106 to turn off retort manifold heater after filling with first reagent. Otherwise, an action is inserted at 107 prior to the first step to fill retort with the first reagent to ensure tissue is covered as soon as possible after schedule is accepted. At 108 an action is inserted to perform a pressure test before the fill commences. At 109 stations or, in particular, reagents are allocated to steps using a method such as Select Reagent described herein. At 110 actions for pressurizing, venting and associated retort actions are notionally allocated. At 111 checks are made of selected reagents for compatibility and a warning is given to a user where appropriate at 112. The user may then edit the protocol to skip steps or change step lengths as at 119. If the compatibility of these edits is ok 124 the protocol workflow is repeated from step 103, otherwise an error is displayed for rules failure at 128. If there are insufficient resources determined at 113, this is logged and the scheduling of the protocol is aborted at 114, 116. If thresholds are exceeded, for example purity, this is logged at 115 then protocol checks are performed at 117 and the protocol is presented to a user for confirmation at 118 with any appropriate warnings giving the user opportunity to modify timings at 121 or edit protocol steps as at 119. The user may decide to abort at 125 or confirm the schedule at 123 giving a successful scheduling outcome for the protocol.

The following should be noted.

In the course of changing reagents, the particular step in changing reagent includes provision for an air flush before and after the change. Thus, time taken for the air flush before changing reagents should be subtracted from the step length.

The first step will fill the retort and hold until the change reagent time. This time will be fixed whereas the step length of the first step may vary. This variation of step length will depend on the time the schedule is accepted. Temperature and agitation will only be applied if the first step is wax. Wax will be held at the wax standby temperature and agitation set to the value in the protocol for the first step. Pressure will only apply once the protocol step properly commences.

Fluidics clashes should take account of the air flush following a change reagent step Ordinarily, it would be assumed that retort heating commences after a flush and prior to a drain reagent.

Protocol actions may include any of the "atomic" fluidic actions specified by system software requirements or specific monitoring action. These may include fill retort, change reagent, start background monitoring, wait, and stop background monitoring.

It is preferred that the system provides a warning when a protocol that uses reagent selection method by group is scheduled and there are not more bottles of a reagent group than there are steps in a protocol using those bottles.

Schedule Second Running Protocol

It is envisaged that a second protocol may be required that superimposes or even overrides an existing protocol running on the system. A system request may be introduced and this may result in pausing the running protocol, running the scheduled first retort with the current protocol and rescheduling the remainder of the running protocol as a "scheduling subsequent retort"

Protocols already scheduled that do not drain on completion may lock out use of that reagent for 1 hr after the completion of the protocol unless the retort is drained previously.

Figure 14:
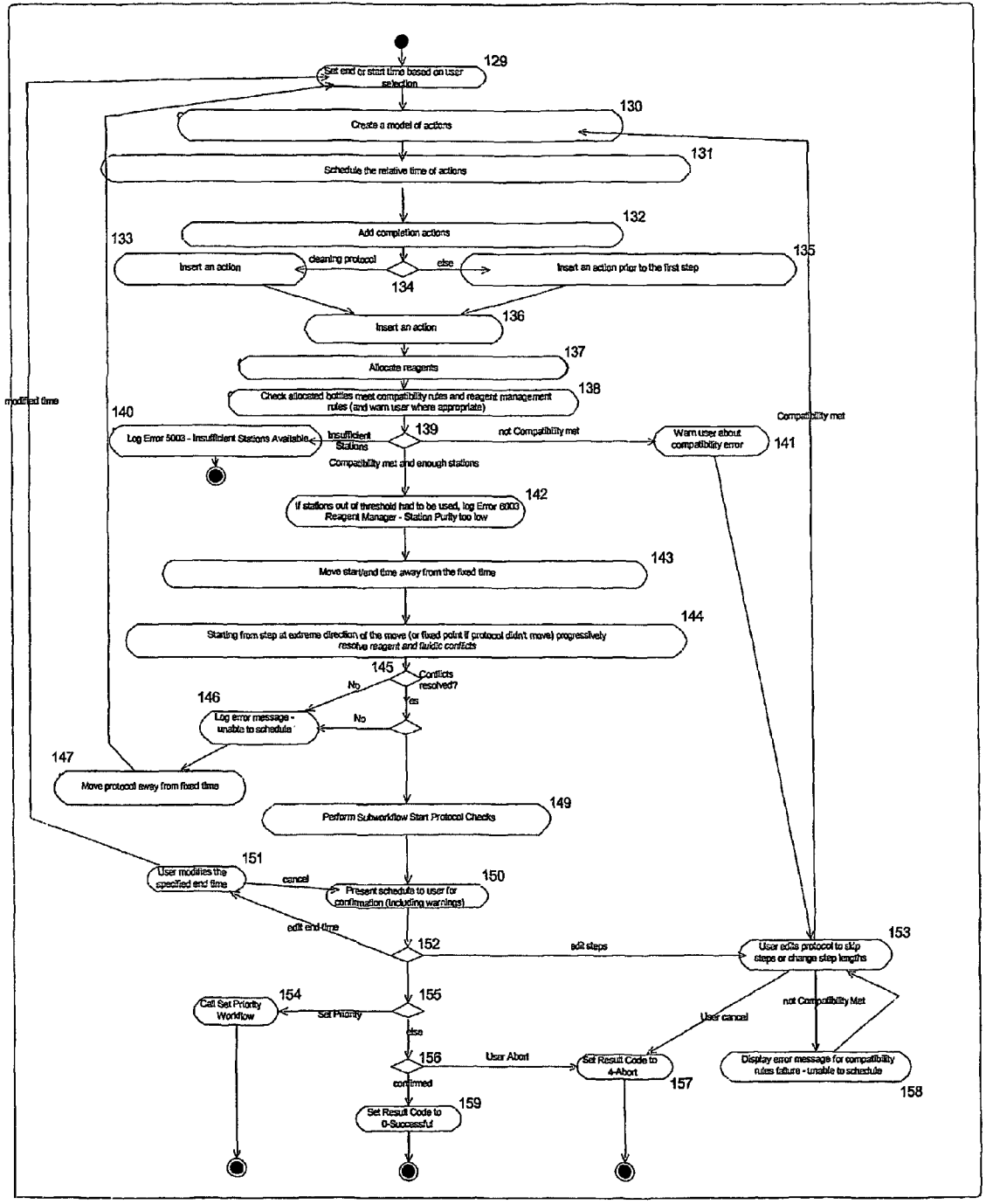
FIG. 14 is a flow chart of an exemplary workflow for scheduling a second protocol in conjunction with a single protocol.
Figure 15:
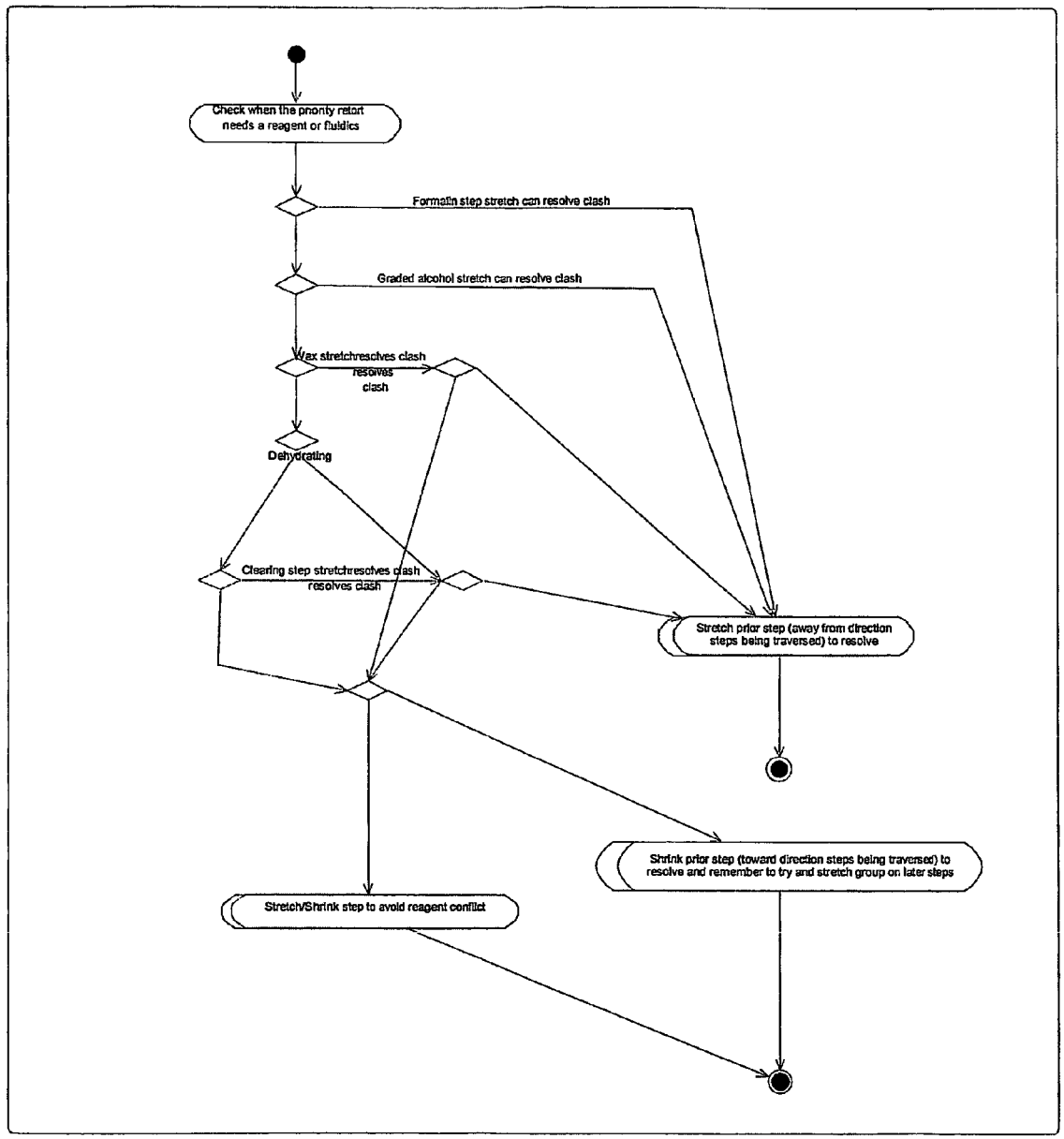
FIG. 15 is a flow chart of an exemplary workflow for resolving conflict between protocol steps scheduled in accordance with the workflow of FIG. 12.

With particular reference to FIG. 14 as with the scheduling of a single protocol the workflow commences with a user defined or set end time or start time at 129. At 130 a model of protocol actions is created. Again these may include estimated durations, relative to the specified start or end time of the run. Examples are fill, change reagent, retort manifold heat and retort heat using Select Station for station selection as in FIG. 13. At 131 the relative timing of modelled actions is scheduled taking account of step length, time of action and ensuring retort manifold is heated prior to the first wax step. As with the single protocol scheduling if the first protocol step is wax the workflow ensures that retort heaters are set to standby temperature at same time. Completion actions are determined at 132 to establish the concluding protocol conditions including turning off Retort Manifold heaters if specified temperature is ambient and draining the retort if this is specified. From this point the steps 133 to 136 are the same as in the single protocol scheduling of FIG. 13. At step 137 an allocation step is performed as in the workflow of FIG. 13. However, now there is a requirement to minimise any conflict that may occur from the second protocol and its steps, which are to be scheduled for the other retort. The priority setting and conflict resolution workflow of FIG. 13 achieve this. Given that a priority is attributed to one of the retorts, the workflow of FIG. 13 provides the user with choices with regard to shortening or lengthening protocol steps with preference based on the priority allocated. In the workflow of FIG. 13 a lengthening of steps is indicated by the "stretch" actions and a shortening of a protocol step is indicated by a "shrink" action. These stretch and shrink actions are possible based on the selected reagents for each of the protocol steps indicated. The methodology of the conflict resolution of the workflow in FIG. 15 may then be repeated as necessary in the scheduling workflow of FIG. 14. For example, conflict resolution is drawn upon again at steps 143 where a previously fixed start/end time may be moved to minimise reagent conflict and without changing time between steps. For example, if initially it appears that moving a time earlier would mean that a retort needs to be already running then the workflow shifts to start later and accordingly extend or stretch the initially requested end time. Step 144 of FIG. 14 provides an iterative progression of conflict resolution in protocol steps. Only if conflicts are resolved at step 145 does the workflow move on to perform the protocol checks for presenting the decided protocol schedule to the user for confirmation. Otherwise an unable to schedule is notified at 146 and the second or lower priority protocol is moved away from it originally fixed time, by say 10 minutes, and the workflow returns to the beginning at step 129. The workflow in all other respects is similar to that of FIG. 13.

Figure 16:
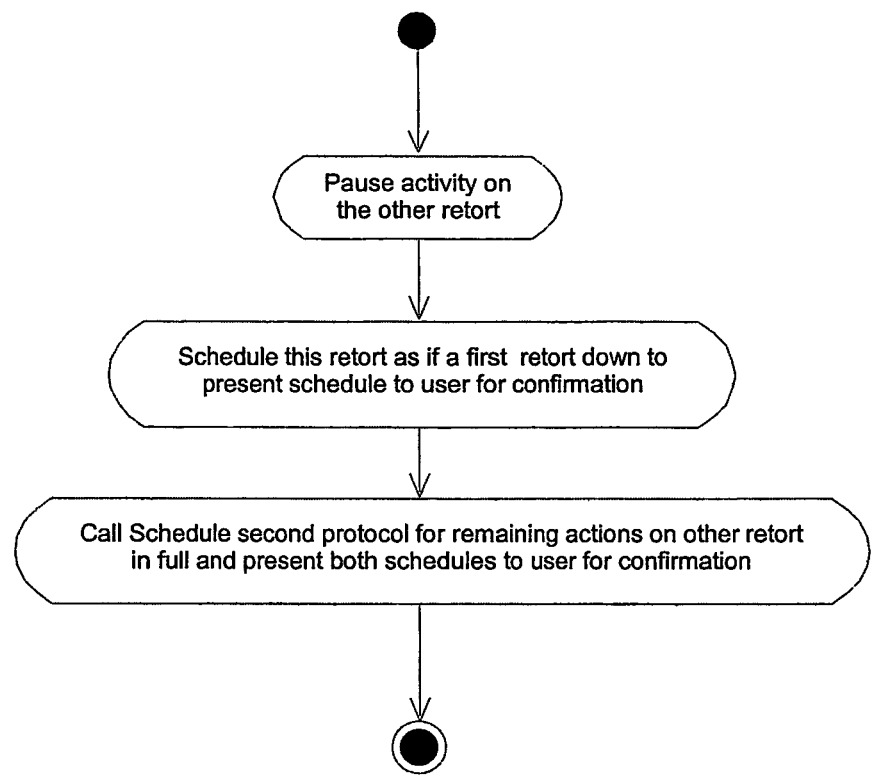
FIG. 16 is a flow chart of an exemplary workflow for setting a priority of a protocol.

The priority setting mechanism is shown by the exemplary workflow of FIG. 16. Ordinarily, a protocol that is up and running will take priority over a protocol yet to be run. Upon being presented with a second protocol to schedule, the first step is to pause activity on the other retort used for the second protocol. There is no need to halt fluidics actions. All that is required is to stop executing new protocol actions. Upon pausing, the workflow then proceeds to schedule the second retort's protocol as if it is the only protocol to be managed. This may be done in accordance with the workflow of FIG. 13, ie schedule a protocol. Finally in the third step of FIG. 16, the workflow of FIG. 14 may be used to schedule a second protocol of the remaining actions of the paused protocol to be run on the first retort. Both schedules of the first and second retorts are then presented to the user for confirmation. In this third step, any remaining actions are removed before scheduling, however, they are stored in case the user doesn't confirm the schedule. The remaining steps are scheduled taking account of where the protocol is at in the current step.

Thermal Systems

The inventor has recognised a link between faster heating and accelerated or faster tissue processing. Shorter processing times are becoming important for the treatment of tissue samples as, for example, medical practitioners are increasingly focusing on rapid patient diagnosis. In the course of seeking solutions to the shortcomings of the related art, the inventor conducted a large number of trial experiments to determine variables, which may have an impact on tissue processing times. These experiments were directed, for example, to an examination of heating times, temperatures in the processing environment, reagent agitation, vacuum levels, pressure levels and fill and drain times for the tissue processor. The inventor has found that temperature is an important factor in determining processing times. With respect to temperature, the inventor has recognised that there are two aspects for consideration.

Firstly, the time to reach a target processing or operating temperature is considered. Tissue processing is greatly accelerated at relatively high temperatures; for example, there is a marked difference in the time required to effectively process tissue specimens at room temperature compared to say 40° C. The inventor has recognised that, for a given protocol step or sub-procedure, if the time in which a tissue sample is exposed to the operating temperature is maximised by shortening the heat up time of the processor component containing the sample then the overall sub-procedure time may be reduced accordingly. For example, using a related art tissue processor, in a one hour step it may take up to 40 minutes to reach the operating temperature for the tissue processing step. The present invention may reduce that heat up time from 40 minutes to 10 minutes, which in turn may allow a reduction in the overall step time from 1 hour to approximately 40 minutes.

The second aspect of temperature considerations relates to the actual operating temperature that is reached. Accordingly, the inventor has recognised that with a higher operating or processing temperature the reduction in overall step time follows in direct relationship. In other words, a small increase in operating temperature may equate to a significant reduction in step time. It follows that by allowing the tissue processing steps to be run at higher temperatures a reduction in processing time may be achieved. However, it should be noted that to make it feasible to function with higher operating temperatures, it is important to accelerate the heat up time otherwise step times would be extended. For example, to attain a relatively high operating temperature on a related art processor it may be necessary to take up to 1 hour to reach a modest temperature of 55° C. using conventional heat up methodologies.

Accordingly, embodiments of the present invention provide a method of accelerating the processing of histological tissue samples comprising the steps of:

sensing the temperature of a selected component of a tissue processor with a first temperature sensor operatively connected to the selected component;

heating the selected component with at least one heating device operatively connected to the selected component;

wherein the at least one heating device is maintained at a temperature at or above a desired operating temperature of the selected component until the first temperature sensor senses the desired operating temperature.

Advantageously, the above method may further comprise the step of:

sensing the temperature of the at least one heating device with a second temperature sensor operatively connected to the at least one heating device so as to allow the at least one heating device to be operated at its maximum operating temperature in order to minimise the time required for the at least one heating device to heat the selected component to the desired operating temperature.

Figure 21:
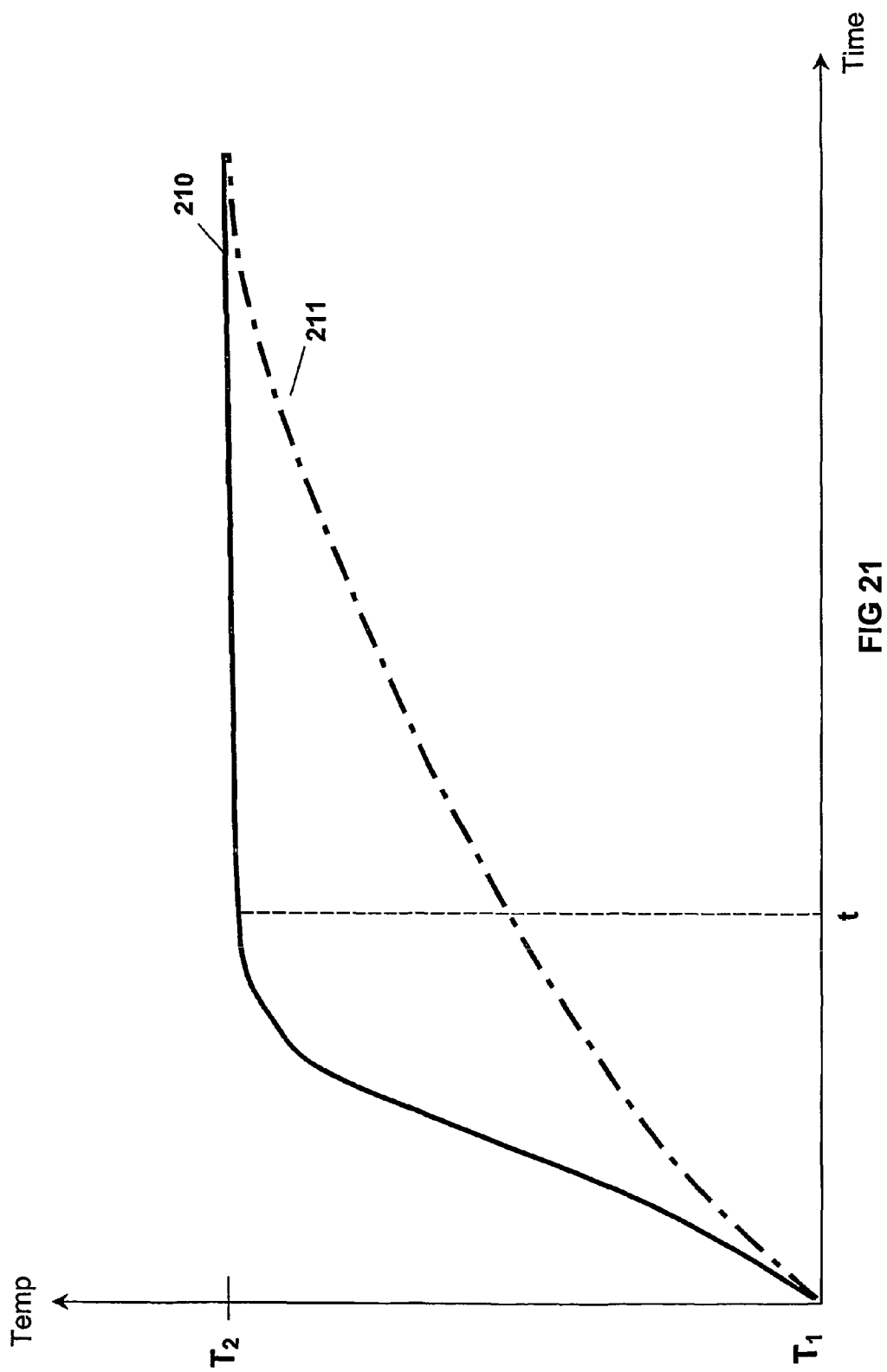
FIG. 21 is a graph of temperature against time depicting the heat up phase of a retort of a tissue processor and showing the temperature curves of a retort heated according to a preferred embodiment of the present invention and a method according to the related art, respectively.

As an illustrative example, FIG. 21 shows heat up times for a retort using the methods of the present invention, shown by curve 210, and using heating methods of related art, shown by curve 211. In a first example, the above method of the present invention was followed using a retort filled with ethanol and a stablised operating temperature, $T_2$, of 55° C. was obtained after a time, t, of 5 minutes. Curve 211 shows that the related art heat up methods utilising temperature sensors operatively connected only to heater mats of a retort, had not reached a stable operating temperature until a considerable time after 5 minutes, in fact, these were closer to 40 minutes. Furthermore, in the related art it appears that temperature stratification in the retort is a significant disadvantage. Temperature stratification, in which a temperature difference between the top and bottom regions of a heated retort is exhibited, of up to 8° C. has been measured in a number of related art tissue processors.

In a second example, the inventor conducted a test to determine whether a retort heating system in accordance with the present invention would perform to required specifications. The test was conducted with the use of an agitator stirring the contents of a retort and such agitation is recognised as a common feature of tissue processors. A retort is filled to a level of 3.8 liters with water and heated from a start temperature $T_1$ of 25° C. to an operating temperature $T_2$ of 85° C. with the agitator running at its maximum speed. The system was allowed to remain at the operating temperature $T_2$ for at least ½ hour. Both the initial or start temperature $T_1$ and the final or operating temperature $T_2$ was tested with independent thermocouple measurements. This test using water was repeated with an initial start temperature $T_1$ of 28° C. and a final operating temperature $T_2$ of 55° C. The stabilised heat up time, t, of water to $T_2$=85° C. from $T_1$=25° C. was measured at t=17 minutes. The stabilised heat up time, t, of water to $T_2$=55° C. from $T_1$=28° C. was measured at t=7 minutes 10 seconds. It was estimated that the heat up time of water to $T_2$=55° C. from a temperature $T_1$=20° C. is 9 minutes 17 seconds. Significantly, using the thermal resource management methods of the present invention, temperature stratification in the retort measured at the operating temperatures was 0.1° C. More detailed description of the thermal resource management methods is given below. Generally, the methods of heating and the control and management of thermal resources of a tissue processor disclosed herein may be selectively applied to any suitable component of a tissue processor that conveys or holds reagents for the tissue processing. For example, the invention may be applied to one or more tissue processing retort valves; one or more tissue processing wax storage baths or, one or more tissue processing fluid lines connecting one or more retorts and wax storage baths.

In the preferred embodiment, for each retort there is one heater, comprising a number of connected heater mats for each retort. Equally, as would be recognised by the person skilled in the art, when a single retort tissue processor is used, there is generally one heater comprising a number of heater mats. Further, the thermal systems described hereinbelow may be applicable to a tissue processor having only one retort with the appropriate parameters, as would be recognised by the person skilled in the art. The wax bath may comprise eight heaters, four bath wall heaters, one for each chamber, and four bath bottom heaters, one for each wax chamber. Additional heaters may be provided to heat the wax bath valve manifold, the wax transfer lines, the retort valve manifolds and the contamination sensor. When heating a device or component of the tissue processor, two different modes of power application may be used, namely, "ramping" and "maintaining". Ramping means a higher power is applied to the heater mats to try and "ramp" up the heat very quickly. Power consumption is a lot higher during ramping and so, in the case of the retorts, only one retort should have its heaters in ramp mode at any time. Maintaining usually occurs after ramping when lower power is required to maintain the heat in the device. Preferably, two temperature sensing modules are provided on each retort. The first may be attached to the back of a heater mat and measures the heater mat temperature. By keeping the heater mats at a constant temperature it is possible to keep the liquid temperature constant once steady state conditions have been reached. The second sensor may be mounted directly to the retort wall away from the heater mats and is used to measure the liquid temperature.

The background thermal routines or workflows included are preferably called approximately once per second although faster and much slower frequencies could be tolerated. Frequencies as low as one call every 5 seconds should not have a significant effect on heater performance although a FPGA watchdog will probably have to be strobed more frequently than this, while the electronics is actually carrying out the switching at approximately a 5 Hz rate so that calling frequencies above this rate will have no effect.

These background routines include the Heater manager, the Heater Power Manager and the heater controllers themselves.

The heater controllers and the heater power manager may communicate by way of flags. Each heater controller has two flags, which it sets as requires. The first of these is the "Power Request" flag. This flag is set whenever a heater has a non-zero target temperature set. The second flag is the "Ramp Power Request" flag, which is used whenever the heater is not close to its set temperature. Finally retort heaters have a maximum power value, which they may reduce when they have a fault condition, which limits the amount of power they may safely accept. All of these values may only be set by the heater involved and should be read-only to the heater management routines.

A heater manager responsible for monitoring the operation of the heaters and temperature modules in the system may be employed and preferably faulty temperature modules are noted and where possible corrective action taken to overcome these problems.

Heater Power Manager

The heater power manager is responsible for allocating power to the different heaters on the instrument. If all the heaters on the instrument were switched on at once then the instrument would draw more power than was available from the power point. This routine analyses the various requests for power in the instrument and then allocates the available power to the most appropriate locations.

In certain fault situations the heater manager will also limit the available power to a heater to prevent heater mats from overheating.

Inputs

This routine has no passed inputs but looks at the status flags of the various heaters in the system Configuration Values Various Power allocation tables appropriate for each power supply and operating condition of the instrument are configured for use.

Figure 17:
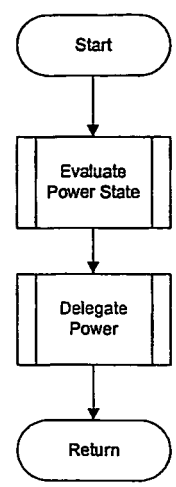
FIG. 17 is a flow chart of an exemplary workflow for managing resource heating power in accordance with a preferred embodiment of the invention.

FIG. 17 is a flow chart of an exemplary heater power manager workflow. The workflow comprises effectively, two other workflows or subflows, namely, an evaluation of power states to determine the current status of thermal resources. Secondly, there is a subflow for delegating power based on the determinations of the current power states found in the evaluate power state workflow.

Evaluate Power State Workflow

Figure 18:
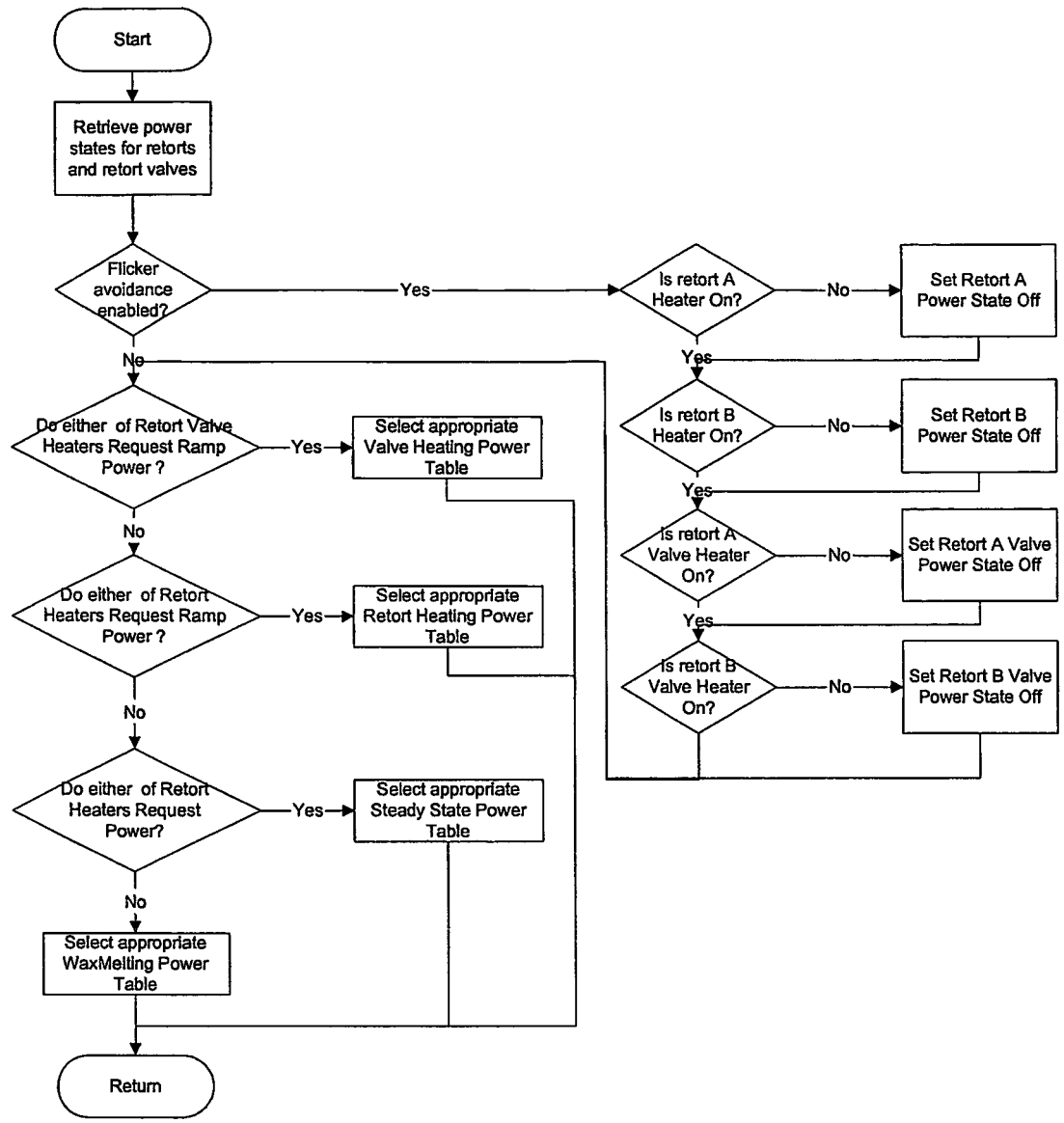
FIG. 18 is a flow chart of an exemplary workflow for evaluating power states in accordance with the workflow of FIG. 17.

FIG. 18 is a flow chart of an exemplary workflow for evaluating power allocations. Firstly, power states for retorts and retort valves are retrieved. A straightforward determination of on/off heater states may be performed in the case of flicker avoidance being enabled. Then the thermal resources are interrogated as to whether power requests have been signalled (ramping or maintaining power). Upon this determination appropriate steady state or "heating" power tables are selected for maintaining and ramping power requests, respectively. The appropriate values to be allocated within the tables would be a selection of power values as understood by the person skilled in the art.

Delegate Power Workflow

Figure 19:
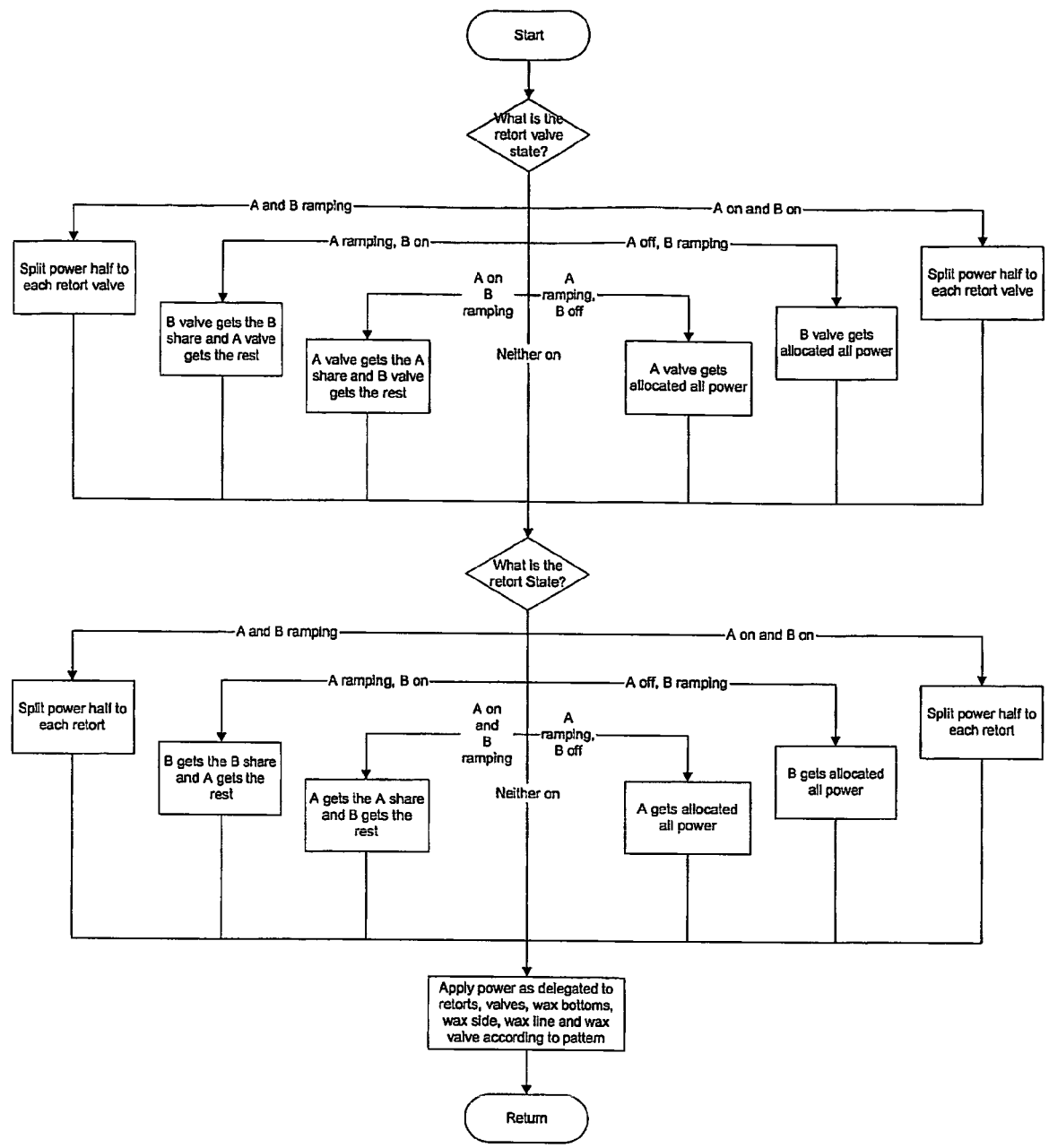
FIG. 19 is a flow chart of an exemplary workflow for delegating power in accordance with the workflow of FIG. 17.

FIG. 19 is a flow chart of an exemplary workflow for delegating power to thermal resources. Each component, for example a retort valve and in turn a retort is queried for its state determined by the evaluating workflow of FIG. 18. Based on the evaluation conducted, the power is then distributed on a normalised or weighted basis to each of the tissue processor component heaters in accordance with their respective states.

Temperature Measurement

GetRetortTemperature

The purpose of this workflow is to allow high level functions to get the appropriate temperature reading from a retort based on its current control algorithm. Trying to read the retort temperature from the temperature module directly will cause problems in various fault conditions and also, if the retort is not full.

Passed Outputs
    Combined temperature reading
    Fault conditions
    Sensor1 temperature reading
    Sensor2 temperature reading Result Codes

| Result Code | Meaning |
| --- | --- |
| 0-Successful | Temperature successfully calculated |
| 1-Unsuccessful | Valid Temperature could not be returned |

Figure 22:
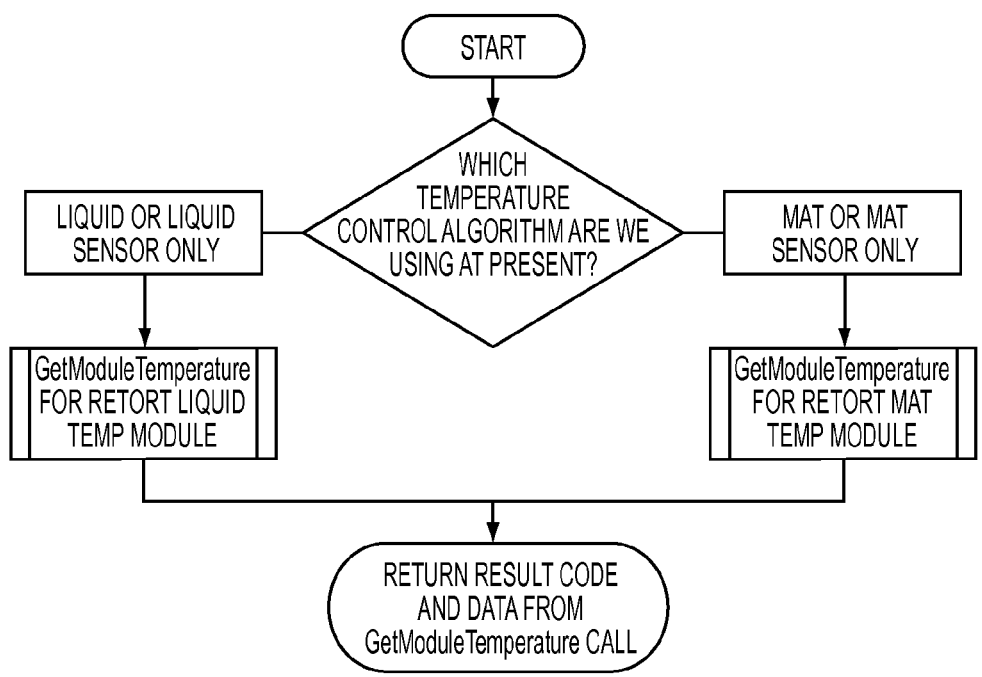
FIG. 22 is a flowchart describing a routine for. GetRetort Temperature workflow.

The flow chart of FIG. 22 describes an example routine for the GetRetortTemperature Workflow. The flow chart is by way of example, only.

GetModuleTemperature

The purpose of this workflow is to get the temperature reading from one of the temperature sensing modules located on the instrument. Each module has two individual sensing elements and the readings from each element must be evaluated and combined to give the output reading.

Passed Outputs
    Combined temperature reading
    Fault conditions
    Sensor1 temperature reading
    Sensor2 temperature reading Configuration Values Result Codes possible

| Result Code | Meaning |
| --- | --- |
| 0-Successful | Temperature successfully calculated |
| 1-Unsuccessful | Valid Temperature could not be returned |

Figure 23A:
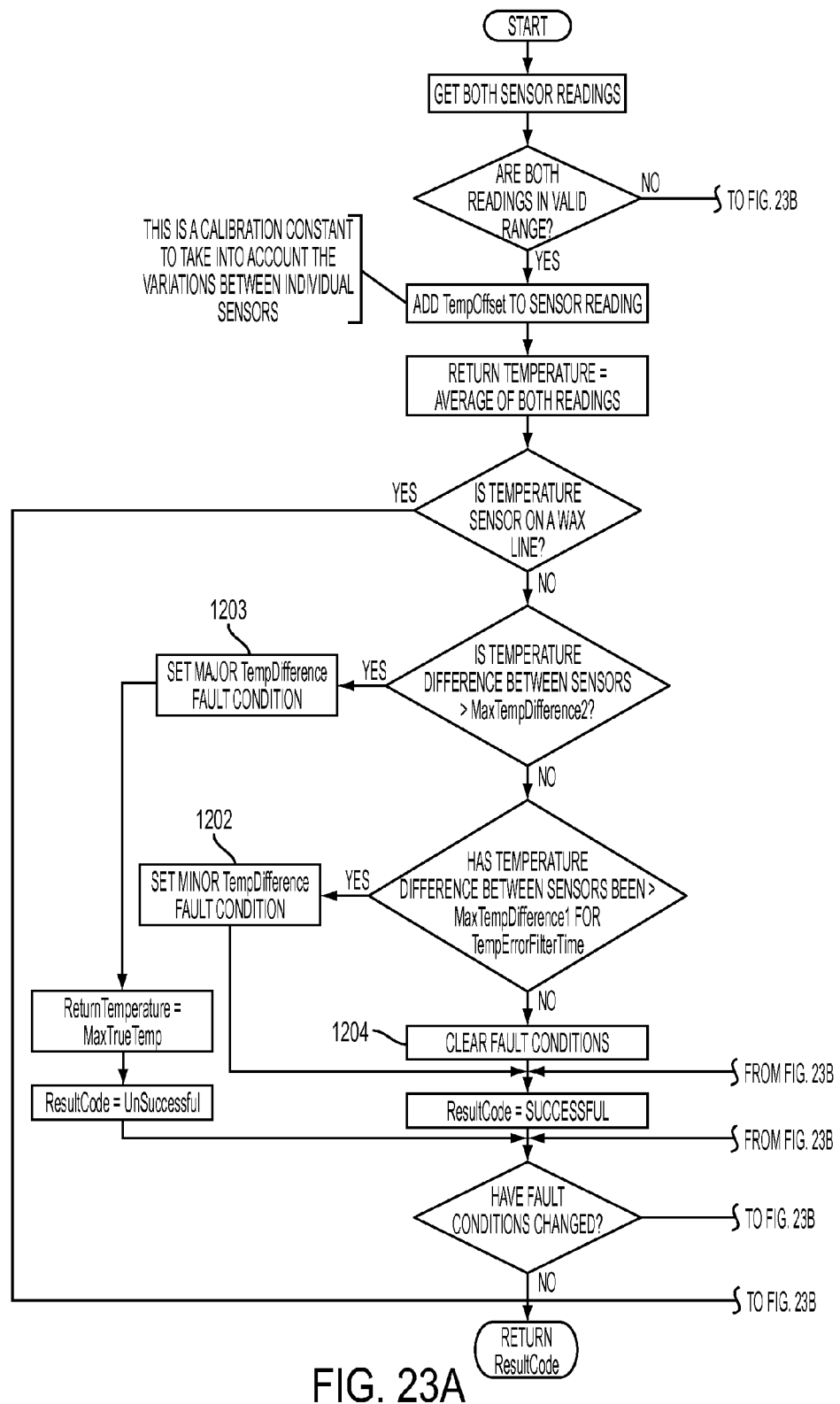
FIGS. 23A and 23B represent a flowchart showing how a Module temperature may be ascertained.
Figure 23B:
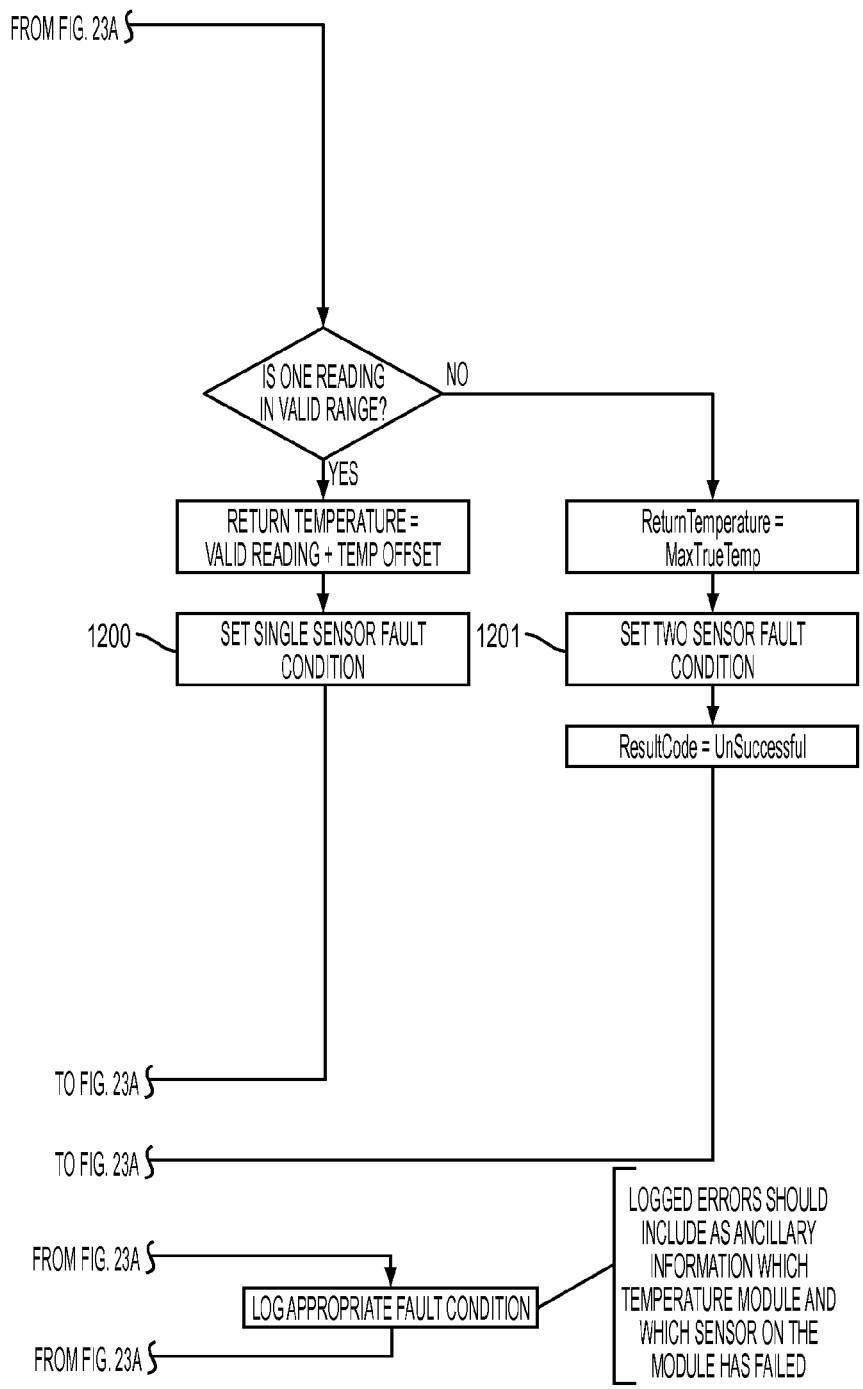

An exemplary flow chart found in FIGS. 23A and 23B describes how a Module temperature may be ascertained. The flow chart found in FIGS. 23A and 23B is by way of example, only.

As would be appreciated by the person skilled in the art, other heater modules within the instrument, apart from the retorts or wax baths, may be controlled with separate routines. The person skilled in the art would also appreciate that other routines may be called into action. For example, a routine may be employed to change the temperature control module used to control a heater. This would allow a wax chamber to continue in operation despite the failure of a temperature sensor by linking the control of the wax chamber heater outputs to that of a different wax chamber. Equally, a routine may be employed to retrieve the duty cycle value that may be continuously calculated by the heater control routine. This information may be useful in testing and diagnostic functions and furthermore may be used to estimate whether a wax bath is molten or not.

Retort Heaters

Heater Control

This routine is individually for each retort and is repeated approximately every second.

Passed Parameters
    None

Configuration Values

| Identifier | Default Value | Meaning |
| --- | --- | --- |
| TempTolerance | 0.1 C. | This is the control tolerance around the heater set point |

| Identifier | Default Value | Meaning |
| --- | --- | --- |
| MinTrueTemp | 5 C. | Temperatures below this value are discarded as being incorrect due to sensor being disconnected or a fault shorting the output to ground |
| MaxTrueTemp | 140 C. | Temperatures above this value are discarded as being incorrect due to a sensor fault causing the output to be connected to the supply voltage |
| MaxTempDifference1 | 4 C. | Maximum temperature difference between two individual sensors before issuing a warning error |
| TempErrorFilterTime | 6 min | Time temperature difference must persist before flagging a minor error |
| MaxTempDifference2 | 10 C. | Maximum temperature difference between two individual sensors before issuing a fault error |
| TempOffset | 0 C. (Direct Mounting) | Offset value added to scaled sensor output to convert to absolute ° C. |
| | 3 C. (Heater Mats) | Offset value added to scaled sensor output to convert to absolute ° C. Heater mats require a different value as the mounting holes for the temperature sensors make the mounting point for the temperature sensors the coldest point on the mat. |

-continued

| Identifier | Default Value | Meaning |
|---|---|---|
| RampRequestTolerance | 3 C. | At temperatures this amount below the heater setpoint the heater will request ramp power |
| DutyCycleAverageTime | 5 minutes | Time over which to calculate average heater duty cycles |

Result Codes possible

| Result Code | Meaning |
|---|---|
| 0-Successful | Heater was successfully controlled |
| 1-Unsuccessful | Temperature Sensor Failure/Heater Switched Off |
| 3-Limping | Heater is Limping |

Figure 20:
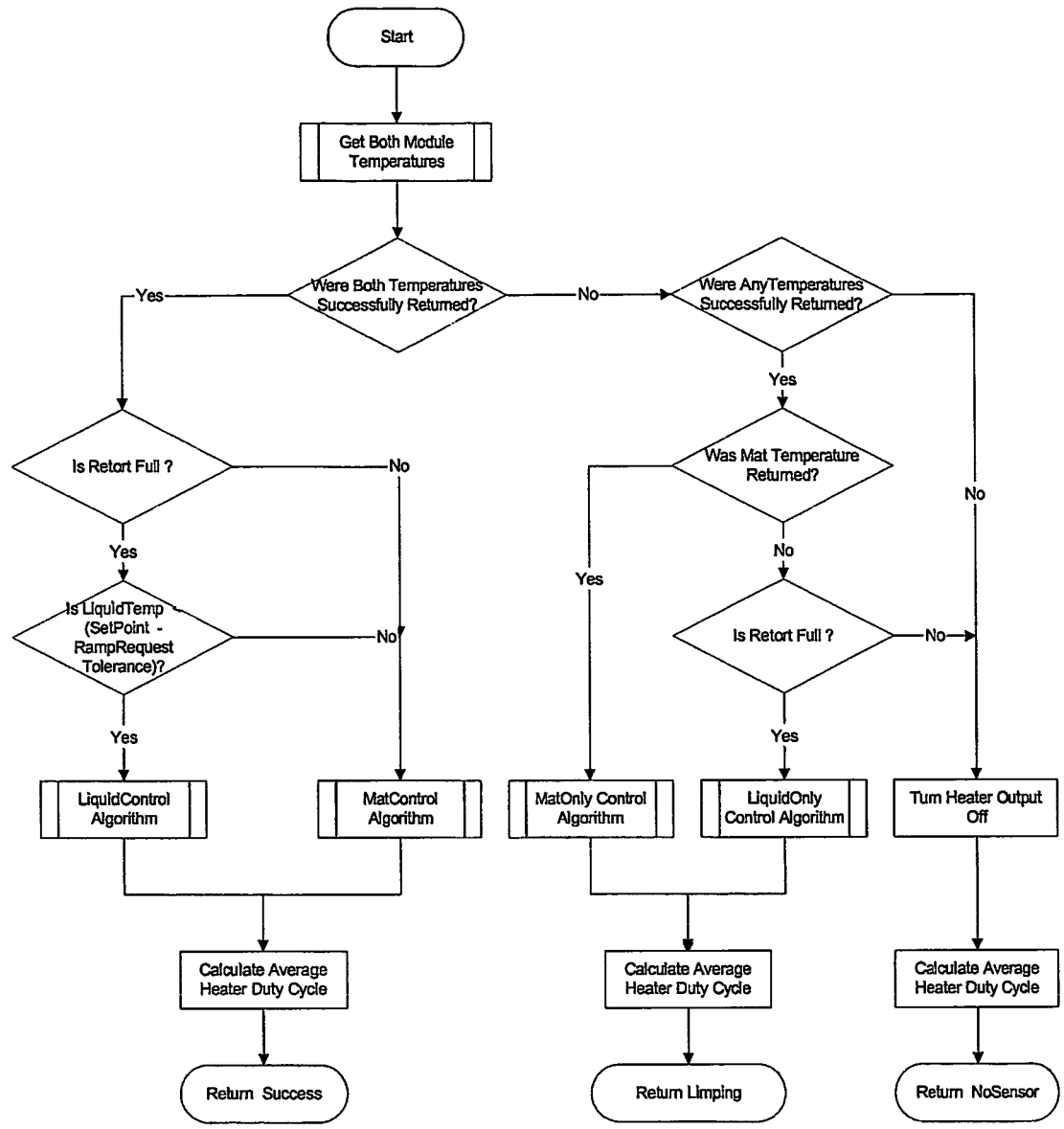
FIG. 20 is a flow chart of an exemplary workflow for controlling heaters in a tissue processor in accordance with a preferred embodiment of the invention.

FIG. 20 is a flow chart of an exemplary work flow for retort heater control. In this example, the workflow is operated for each retort individually, as noted. At first, temperatures are probed from all temperature modules by way of the GetModuleTemperature workflows. Based on whether or not successful temperature readings were ascertained, the fill state of the retort, the location of the temperature modules that returned readings and the temperature of any liquid that may be in the retort, an appropriate heater control algorithm is selected. If there are no returned temperature readings heater output is turned off. This is also the result when no mat temperature is returned and the retort is not full. Accordingly, where there is liquid in the retort and it is determined that rapid heating is required or a mat temperature is not available, a liquid or liquid sensor only algorithm is utilised. Likewise for situations where there is no full retort or temperature maintenance is determined then a mat/mat sensor only algorithm may be used. These algorithms are explained in further detail below.

Liquid Control Algorithm

This algorithm is used for the rapid heating of liquids in the retort. It should only be used when there is liquid in the retort otherwise very high retort wall temperatures may result.

Configuration Values

| Identifier | Default Value | Meaning |
|---|---|---|
| TempTolerance | 0.5 C. | This is the control tolerance around the heater set point |
| RampRequestTolerance | 3 C. | At temperatures this amount below the heater set point the heater will request ramp power |
| MaximumMatTemperature | 100° C. | Maximum allowable mat control temperature |

Figure 24:
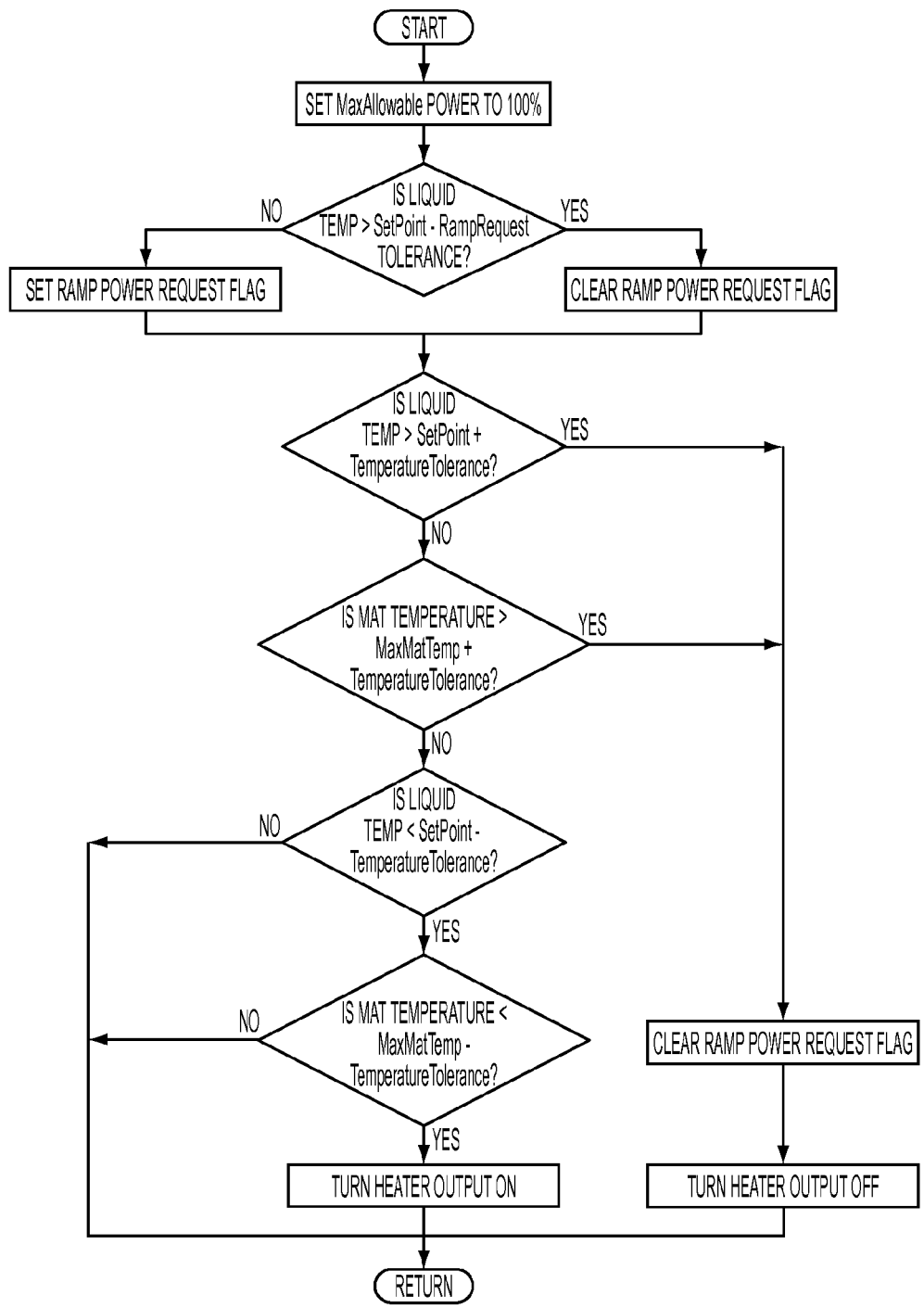
FIG. 24 is a flowchart for a liquid flow control algorithm.

An exemplary workflow for a liquid control algorithm is shown, by way of example, only, in the flow chart found in FIG. 24.

Mat Control Algorithm

This algorithm may be used for the steady state maintenance of liquid temperature in the retort. It may also be used when there is no liquid in the retort for preheating.

Configuration Values

| Identifier | Default Value | Meaning |
|---|---|---|
| TempTolerance | 0.5 C. | This is the control tolerance around the heater set point |
| RampRequestTolerance | 3 C. | At temperatures this amount below the heater set point the heater will request ramp power |

Figure 25:
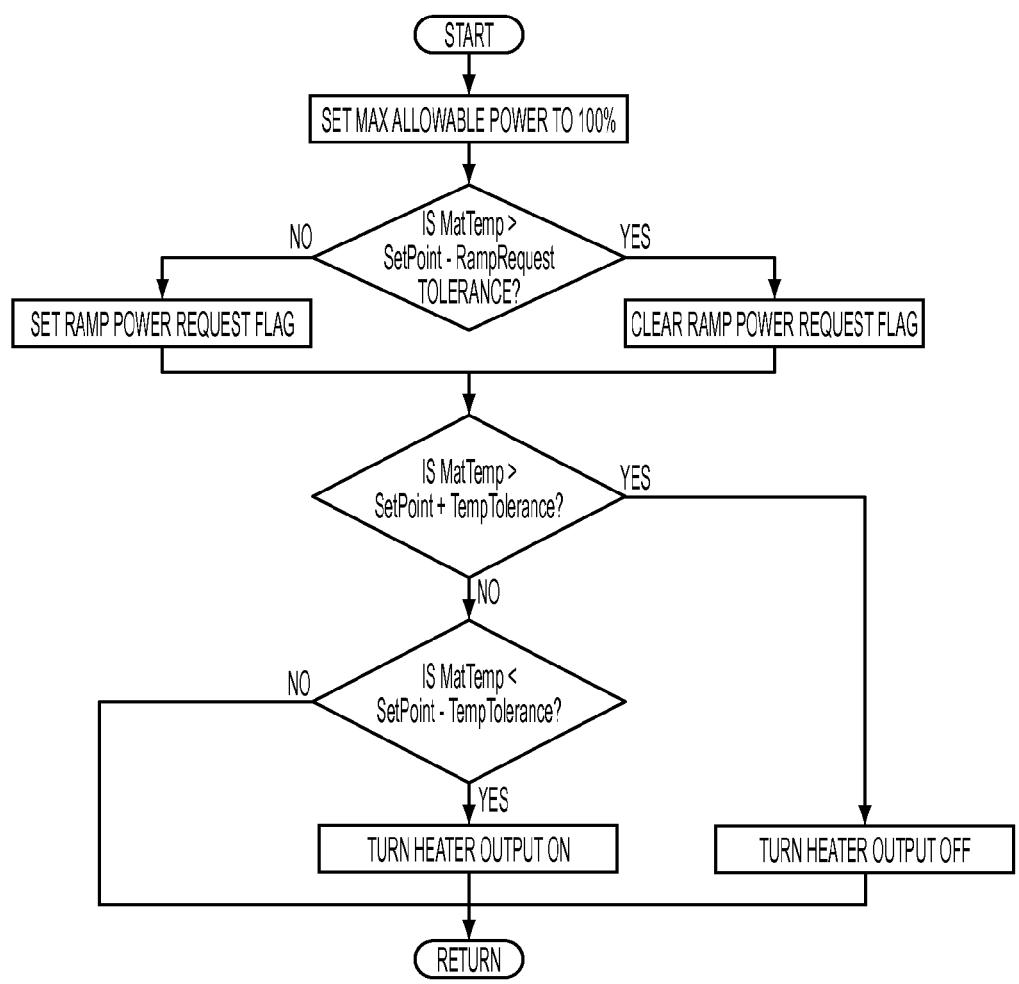
FIG. 25 is a flowchart for a heater mat control algorithm.

An exemplary workflow for a heater mat control algorithm is described in FIG. 25 by way of example, only.

Liquid Sensor Only Control Algorithm

This algorithm may be used for the heating of liquid in the retort when input from the mat temperature sensor is not available. Mat temperatures are limited by reducing the power supplied to the mat as liquid temperature increases. It should not be used to heat an empty retort.

Configuration Values

| Identifier | Default Value | Meaning |
|---|---|---|
| TempTolerance | 0.5 C. | This is the control tolerance around the heater set point |
| RampRequestTolerance | 3 C. | At temperatures this amount below the heater set point the heater will request ramp power |
| FullPowerLimitTemp | 40° C. | Maximum Liquid temperature that will still allow full power from the heater mats without overheating the mats above their limiting temp. |
| HalfPowerLimitTemp | 60° C. | Maximum Liquid temperature that will still allow 50% power from the heater mats without overheating the mats above their limiting temp. |

Figure 26:
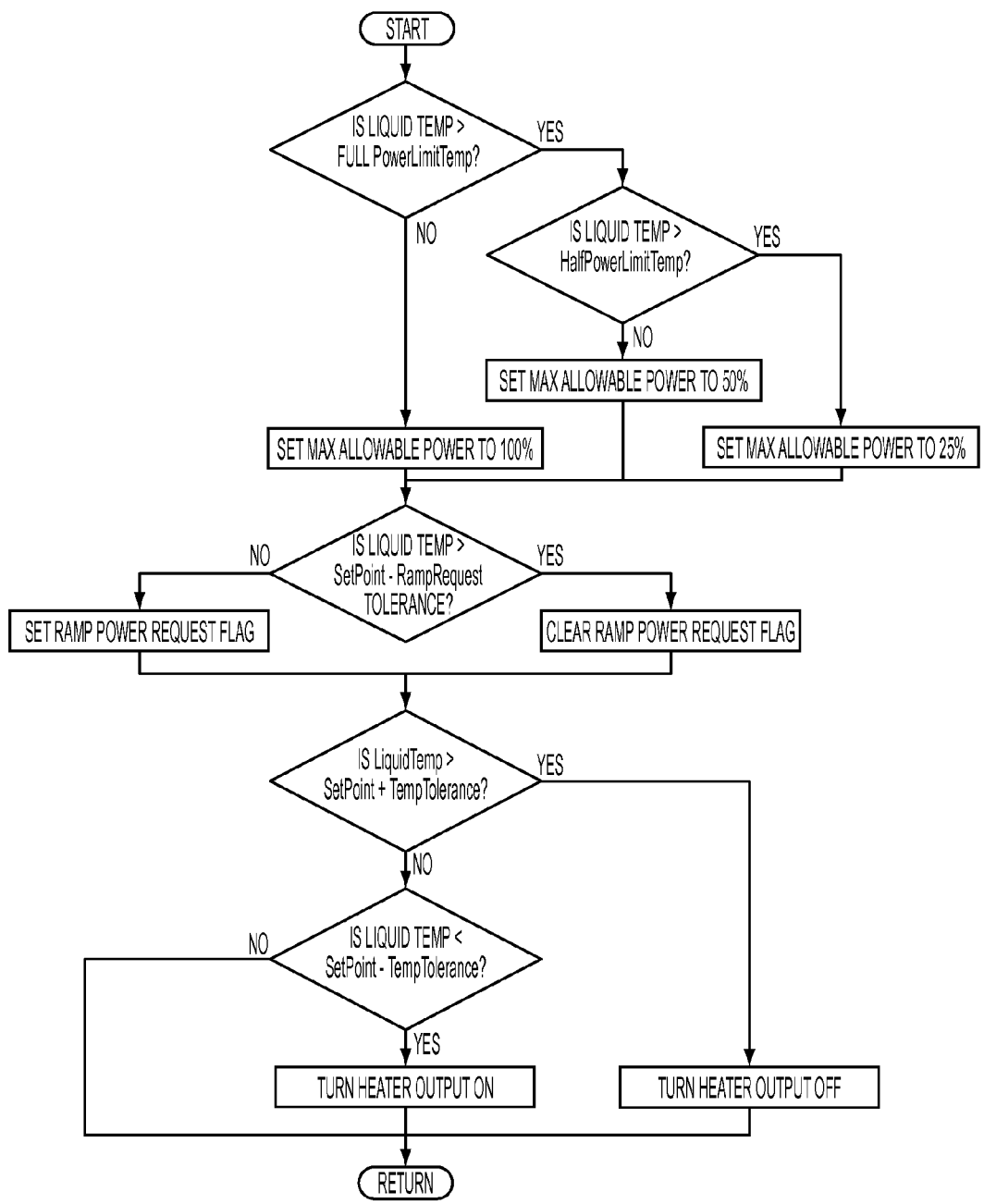
FIG. 26 is a flowchart for a liquid sensor only control algorithm.

An exemplary workflow is described in FIG. 26 which illustrates a flow chart of a liquid sensor only control algorithm.

Mat Sensor Only Control Algorithm

This algorithm may be used for the heating of liquid in the retort when input from the liquid temperature sensor is not available. The standard mat control heating algorithm may be used in this case.

While this invention has been described in connection with specific embodiments thereof, it will be understood that it is capable of further modification(s). This application is intended to cover any variations uses or adaptations of the invention following in general, the principles of the invention and comprising such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures. For example, although a nail and a screw may not be structural equivalents in that a nail employs a cylindrical surface to secure wooden parts together, whereas a screw employs a helical surface to secure wooden parts together, in the environment of fastening wooden parts, a nail and a screw are equivalent structures.

"Comprises/comprising" when used in this specification is taken to specify the presence of stated features, integers, steps or components but does not preclude the presence or addition of one or more other features, integers, steps, components or groups thereof.

The invention claimed is:

1. A method of scheduling tissue processing protocols of a histological tissue processor, the tissue processor comprising at least two retorts selectively connected for fluid communication to at least one of a plurality of reagent resources by a valve mechanism, the method comprising:
   scheduling a plurality of tissue processing protocols, wherein each protocol has at least two steps, to be performed by the at least two retorts;
   resolving conflict between protocol steps allocated respectively to the retorts, comprising the steps of:
   determining a priority for each tissue processing protocol which has at least two steps;
   selectively modifying at least two protocol steps of at least one of the tissue processing protocols based on the determined priority, wherein the selectively modifying the at least two protocol steps includes changing the order of the steps.

2. The method of claim 1, wherein the at least two protocol steps are steps of fixation, dehydration, waxing, defatting, clearing, infiltration, cleaning, or drying.

3. The method of claim 1, wherein selectively modifying the at least two protocol steps comprises stretching the time necessary to complete at least one of the protocol step of the at least two protocol steps.

4. The method of claim 2, wherein selectively modifying the at least two protocol steps comprises stretching the time necessary to complete at least one of the protocol step of the at least two protocol steps.

5. The method of claim 1, wherein selectively modifying the at least two protocol steps comprises shrinking the time necessary to complete at least one of the protocol step of the at least two protocol steps.

6. The method of claim 2, wherein selectively modifying the at least one protocol step comprises shrinking the time necessary to complete at least one of the protocol step of the at least two protocol steps.

7. The method of claim 1, wherein the selectively modifying the at least two protocol steps by changing the order of the steps includes the total time duration remaining unmodified.

8. A method of scheduling tissue processing protocols of a histological tissue processor, the tissue processor comprising at least two retorts selectively connected for fluid communication to at least one of a plurality of reagent resources by a valve mechanism, the method comprising the steps of:
   allocating a tissue processing protocol having at least two steps to each respective retort;
   assigning a priority for each allocated tissue processing protocol;
   selectively modifying at least two protocol steps of the tissue processing protocol assigned with a lower priority, wherein the selectively modifying the at least one protocol step includes changing the order of the steps.

9. The method of claim 8, wherein the at least two protocol steps are steps of fixation, dehydration, waxing, defatting, clearing, infiltration, cleaning, or drying.

10. The method of claim 8, wherein selectively modifying the at least two protocol steps comprises stretching the time necessary to complete at least one of the protocol step of the at least two protocol steps.

11. The method of claim 9, wherein selectively modifying the at least two protocol steps comprises stretching the time necessary to complete at least one of the protocol step of the at least two protocol steps.

12. The method of claim 8, wherein selectively modifying the at least two protocol steps comprises shrinking the time necessary to complete at least one of the protocol step of the at least two protocol steps.

13. The method of claim 9, wherein selectively modifying the at least one protocol step comprises shrinking the time necessary to complete at least one of the protocol step of the at least two protocol steps.

14. The method of claim 8, wherein the selectively modifying the at least two protocol steps by changing the order of the steps includes the total time duration remaining unmodified.

* * * * *

UNITED STATES PATENT AND TRADEMARK OFFICE
CERTIFICATE OF CORRECTION

PATENT NO. : 8,554,372 B2  Page 1 of 1
APPLICATION NO. : 10/573856
DATED : October 8, 2013
INVENTOR(S) : Windeyer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1574 days.

Signed and Sealed this

Fifteenth Day of September, 2015

Michelle K. Lee
*Director of the United States Patent and Trademark Office*